(12) United States Patent
Jansen

(10) Patent No.: US 10,828,074 B2
(45) Date of Patent: Nov. 10, 2020

(54) EXPANDALBE INTRAMEDULLARY SYSTEMS AND METHODS OF USING THE SAME

(71) Applicant: GLOBUS MEDICAL, INC., Audubon, PA (US)

(72) Inventor: David Jansen, Glenmoore, PA (US)

(73) Assignee: Globus Medical, Inc., Audubon, PA (US)

( * ) Notice: Subject to any disclaimer, the term of this patent is extended or adjusted under 35 U.S.C. 154(b) by 9 days.

(21) Appl. No.: 15/956,270

(22) Filed: Apr. 18, 2018

(65) Prior Publication Data

US 2018/0235680 A1    Aug. 23, 2018

Related U.S. Application Data

(63) Continuation of application No. 14/946,939, filed on Nov. 20, 2015, now Pat. No. 9,974,581.

(51) Int. Cl.
*A61B 17/74*    (2006.01)
*A61B 17/72*    (2006.01)

(52) U.S. Cl.
CPC ........ *A61B 17/744* (2013.01); *A61B 17/7216* (2013.01); *A61B 17/7225* (2013.01); *A61B 17/7258* (2013.01); *A61B 17/7266* (2013.01); *A61B 17/7275* (2013.01)

(58) Field of Classification Search
CPC .............. A61B 17/7233; A61B 17/744; A61B 17/7241; A61B 17/7258; A61B 17/7266; A61B 17/72; A61B 17/7291; A61B 17/7225; A61B 2017/681; A61B 17/1725
See application file for complete search history.

(56) References Cited

U.S. PATENT DOCUMENTS

| | | | |
|---|---|---|---|
| 1,105,105 A | 7/1914 | Sherman |
| 1,737,488 A | 11/1929 | Zohlen |
| 2,381,050 A | 8/1945 | Hardinge |
| 2,486,303 A | 10/1949 | Longfellow |
| 3,024,785 A | 3/1962 | Dobelle |
| 3,463,148 A | 8/1969 | Treace |
| 3,695,259 A | 10/1972 | Yost |
| 3,716,050 A | 2/1973 | Johnston |
| 3,759,257 A | 9/1973 | Fischer et al. |
| 4,219,015 A | 8/1980 | Steinemann |

(Continued)

FOREIGN PATENT DOCUMENTS

| | | |
|---|---|---|
| CN | 201987653 U | 9/2011 |
| CN | 202313691 U | 7/2012 |

(Continued)

*Primary Examiner* — Ellen C Hammond
*Assistant Examiner* — Tara Rose E Carter

(57) ABSTRACT

Intramedullary systems, expandable intramedullary nails, expandable anchors, and methods of using the same. The intramedullary system may include an expandable intramedullary nail configured to extend into an intramedullary canal of a long bone and/or one or more expandable anchors configured to extend at an angle transverse to the intramedullary nail. The intramedullary nails and/or anchors may include one or more integrated expansion mechanisms that allow for insertion in a contracted configuration and expansion into a deployed configuration to lock the relative position and prevent axial rotation and translation of the system.

20 Claims, 22 Drawing Sheets

(56) References Cited

U.S. PATENT DOCUMENTS

| | | | |
|---|---|---|---|
| 4,237,875 A | 12/1980 | Termanini | |
| 4,453,539 A * | 6/1984 | Raftopoulos | A61B 17/7258 606/63 |
| 4,493,317 A | 1/1985 | Klaue | |
| 4,524,765 A | 6/1985 | de Zbikowski | |
| 4,590,930 A | 5/1986 | Kurth et al. | |
| 4,651,724 A | 3/1987 | Berentey et al. | |
| 4,683,878 A | 8/1987 | Carter | |
| 4,781,183 A | 11/1988 | Casey et al. | |
| 4,867,144 A | 9/1989 | Karas et al. | |
| 4,923,471 A | 5/1990 | Morgan | |
| 4,966,599 A | 10/1990 | Pollock | |
| 5,002,544 A | 3/1991 | Klaue et al. | |
| 5,041,114 A | 8/1991 | Chapman et al. | |
| 5,116,378 A | 5/1992 | Carbone | |
| 5,151,103 A | 9/1992 | Tepic et al. | |
| 5,259,398 A | 11/1993 | Vrespa | |
| 5,281,225 A | 1/1994 | Vicenzi | |
| 5,364,399 A | 11/1994 | Lowery et al. | |
| 5,372,598 A | 12/1994 | Luhr et al. | |
| 5,387,239 A | 2/1995 | Bianco et al. | |
| 5,397,328 A | 3/1995 | Behrens et al. | |
| 5,415,660 A | 5/1995 | Campbell et al. | |
| 5,423,826 A | 6/1995 | Coates et al. | |
| 5,437,675 A | 8/1995 | Wilson | |
| 5,458,599 A | 10/1995 | Adobbatti | |
| 5,468,242 A | 11/1995 | Reisberg | |
| D365,634 S | 12/1995 | Morgan | |
| 5,480,400 A | 1/1996 | Berger | |
| 5,489,305 A | 2/1996 | Morgan | |
| 5,505,733 A | 4/1996 | Justin et al. | |
| 5,505,734 A | 4/1996 | Caniggia et al. | |
| 5,516,335 A | 5/1996 | Kummer et al. | |
| 5,527,311 A | 6/1996 | Procter et al. | |
| 5,531,792 A | 7/1996 | Huene | |
| 5,536,269 A | 7/1996 | Spievack et al. | |
| 5,578,035 A | 11/1996 | Lin | |
| 5,578,036 A | 11/1996 | Stone et al. | |
| 5,601,553 A | 2/1997 | Trebing et al. | |
| 5,676,667 A | 10/1997 | Hausman | |
| 5,690,631 A | 11/1997 | Duncan et al. | |
| 5,702,481 A | 12/1997 | Lin | |
| 5,709,686 A | 1/1998 | Talos et al. | |
| 5,709,687 A | 1/1998 | Pennig | |
| 5,718,704 A | 2/1998 | Medoff | |
| 5,718,705 A | 2/1998 | Sammarco | |
| 5,746,742 A | 5/1998 | Runciman et al. | |
| 5,766,175 A | 6/1998 | Martinotti | |
| 5,766,176 A | 6/1998 | Duncan | |
| 5,779,706 A | 7/1998 | Tschakaloff | |
| 5,785,712 A | 7/1998 | Runciman et al. | |
| 5,797,914 A | 8/1998 | Leibinger | |
| 5,810,820 A | 9/1998 | Santori et al. | |
| 5,814,048 A | 9/1998 | Morgan | |
| 5,925,048 A | 7/1999 | Ahmad et al. | |
| 5,938,664 A | 8/1999 | Winquist et al. | |
| 5,961,519 A | 10/1999 | Bruce et al. | |
| 5,976,137 A | 11/1999 | Mayer | |
| 5,980,540 A | 11/1999 | Bruce | |
| 6,001,099 A | 12/1999 | Huebner | |
| 6,071,291 A | 6/2000 | Forst et al. | |
| 6,077,265 A | 6/2000 | Werding et al. | |
| 6,093,201 A | 7/2000 | Cooper et al. | |
| 6,096,040 A | 8/2000 | Esser | |
| 6,107,718 A | 8/2000 | Schustek et al. | |
| 6,126,691 A | 10/2000 | Kasra et al. | |
| 6,127,597 A | 10/2000 | Beyar et al. | |
| 6,129,762 A | 10/2000 | Li | |
| 6,152,927 A | 11/2000 | Farris et al. | |
| 6,200,317 B1 | 3/2001 | Aalsma et al. | |
| 6,206,881 B1 | 3/2001 | Frigg | |
| 6,283,969 B1 | 9/2001 | Grusin et al. | |
| 6,309,393 B1 | 10/2001 | Tepic et al. | |
| 6,322,562 B1 | 11/2001 | Wolter | |
| 6,336,929 B1 | 1/2002 | Justin | |
| 6,364,882 B1 | 4/2002 | Orbay | |
| D458,683 S | 6/2002 | Bryant et al. | |
| D458,684 S | 6/2002 | Bryant et al. | |
| 6,443,954 B1 * | 9/2002 | Bramlet | A61B 17/744 606/304 |
| 6,447,513 B1 | 9/2002 | Griggs | |
| 6,533,786 B1 | 3/2003 | Needham et al. | |
| 6,551,321 B1 | 4/2003 | Burkinshaw et al. | |
| 6,554,833 B2 | 4/2003 | Levy et al. | |
| D479,331 S | 9/2003 | Pike et al. | |
| 6,623,486 B1 | 9/2003 | Weaver et al. | |
| 6,648,889 B2 | 11/2003 | Bramlet et al. | |
| 6,669,700 B1 | 12/2003 | Farris et al. | |
| 6,669,701 B2 | 12/2003 | Steiner et al. | |
| 6,712,820 B2 | 3/2004 | Orbay | |
| 6,719,759 B2 | 4/2004 | Wagner et al. | |
| 6,730,091 B1 | 5/2004 | Pfefferle et al. | |
| 6,736,818 B2 | 5/2004 | Perren et al. | |
| 6,767,350 B1 | 7/2004 | Lob | |
| 6,849,076 B2 | 2/2005 | Blunn et al. | |
| 6,866,665 B2 | 3/2005 | Orbay | |
| 6,918,910 B2 | 7/2005 | Smith et al. | |
| 6,955,677 B2 | 10/2005 | Dahners | |
| 6,974,461 B1 | 12/2005 | Wolter | |
| 7,001,387 B2 | 2/2006 | Farris et al. | |
| 7,063,701 B2 | 6/2006 | Michelson | |
| 7,090,676 B2 | 8/2006 | Huebner et al. | |
| 7,128,744 B2 | 10/2006 | Weaver et al. | |
| 7,137,987 B2 | 11/2006 | Patterson et al. | |
| 7,153,309 B2 | 12/2006 | Huebner et al. | |
| 7,179,260 B2 | 2/2007 | Gerlach et al. | |
| 7,250,053 B2 | 7/2007 | Orbay | |
| 7,294,130 B2 | 11/2007 | Orbay | |
| 7,322,983 B2 | 1/2008 | Harris | |
| 7,341,589 B2 | 3/2008 | Weaver et al. | |
| 7,344,538 B2 | 3/2008 | Myerson et al. | |
| 7,354,441 B2 | 4/2008 | Frigg | |
| 7,530,981 B2 | 5/2009 | Kutsenko | |
| 7,604,657 B2 | 10/2009 | Orbay et al. | |
| 7,632,277 B2 | 12/2009 | Woll et al. | |
| 7,635,381 B2 | 12/2009 | Orbay | |
| 7,637,928 B2 | 12/2009 | Fernandez | |
| 7,655,029 B2 | 2/2010 | Niedernberger et al. | |
| 7,655,047 B2 | 2/2010 | Swords | |
| 7,670,339 B2 | 3/2010 | Levy et al. | |
| 7,695,471 B2 | 4/2010 | Cheung et al. | |
| 7,695,472 B2 | 4/2010 | Young | |
| 7,717,946 B2 | 5/2010 | Depen et al. | |
| 7,722,653 B2 | 5/2010 | Young et al. | |
| 7,740,648 B2 | 6/2010 | Young et al. | |
| 7,753,915 B1 | 7/2010 | Eksler et al. | |
| D622,853 S | 8/2010 | Raven, III | |
| 7,771,457 B2 | 8/2010 | Kay et al. | |
| 7,776,076 B2 | 8/2010 | Grady, Jr. et al. | |
| 7,857,838 B2 | 12/2010 | Orbay | |
| 7,867,260 B2 | 1/2011 | Meyer et al. | |
| 7,867,261 B2 | 1/2011 | Sixto, Jr. et al. | |
| 7,875,062 B2 | 1/2011 | Lindemann et al. | |
| 7,879,036 B2 | 2/2011 | Biedermann et al. | |
| 7,905,910 B2 | 3/2011 | Gerlach et al. | |
| 7,909,858 B2 | 3/2011 | Gerlach et al. | |
| 7,914,533 B2 | 3/2011 | Nelson et al. | |
| 7,931,653 B2 | 4/2011 | Hansson | |
| 7,951,178 B2 | 5/2011 | Jensen | |
| 7,951,179 B2 | 5/2011 | Matityahu | |
| 7,976,570 B2 | 7/2011 | Wagner et al. | |
| D643,121 S | 8/2011 | Millford et al. | |
| 8,007,498 B2 | 8/2011 | Mische | |
| 8,012,155 B2 | 9/2011 | Prygoski et al. | |
| D646,785 S | 10/2011 | Milford | |
| 8,029,506 B2 | 10/2011 | Levy et al. | |
| 8,034,054 B2 | 10/2011 | Griggs | |
| 8,043,297 B2 | 10/2011 | Grady, Jr. et al. | |
| 8,043,299 B2 | 10/2011 | Conway | |
| 8,057,520 B2 | 11/2011 | Ducharme et al. | |
| 8,062,296 B2 | 11/2011 | Orbay et al. | |
| 8,096,991 B2 | 1/2012 | Nijenbanning et al. | |
| 8,100,953 B2 | 1/2012 | White et al. | |
| 8,105,367 B2 | 1/2012 | Austin et al. | |

(56) References Cited

U.S. PATENT DOCUMENTS

| | | |
|---|---|---|
| 8,114,081 B2 | 2/2012 | Kohut et al. |
| 8,118,846 B2 | 2/2012 | Leither et al. |
| 8,118,848 B2 | 2/2012 | Ducharme et al. |
| 8,133,226 B2 | 3/2012 | Chou et al. |
| 8,137,349 B2 | 3/2012 | Soubeiran |
| 8,162,942 B2 | 4/2012 | Coati et al. |
| 8,162,950 B2 | 4/2012 | Digeser et al. |
| 8,167,918 B2 | 5/2012 | Strnad et al. |
| 8,177,820 B2 | 5/2012 | Anapliotis et al. |
| 8,187,327 B2 | 5/2012 | Edidin et al. |
| 8,226,659 B2 | 7/2012 | Rabiner et al. |
| 8,246,661 B2 | 8/2012 | Beutter et al. |
| 8,252,032 B2 | 8/2012 | White et al. |
| 8,252,063 B2 | 8/2012 | Stauch |
| 8,257,403 B2 | 9/2012 | Den Hartog et al. |
| 8,257,405 B2 | 9/2012 | Haidukewych et al. |
| 8,257,406 B2 | 9/2012 | Kay et al. |
| 8,262,707 B2 | 9/2012 | Huebner et al. |
| 8,267,972 B1 | 9/2012 | Gehlert |
| 8,287,538 B2 | 10/2012 | Brenzel et al. |
| 8,317,842 B2 | 11/2012 | Graham et al. |
| 8,323,321 B2 | 12/2012 | Gradl |
| 8,337,495 B1 | 12/2012 | Powlan |
| 8,337,535 B2 | 12/2012 | White et al. |
| 8,343,155 B2 | 1/2013 | Fisher et al. |
| 8,366,711 B2 | 2/2013 | Rabiner et al. |
| 8,382,760 B2 | 2/2013 | Mantovani et al. |
| 8,382,807 B2 | 2/2013 | Austin et al. |
| 8,382,842 B2 | 2/2013 | Greenhalgh et al. |
| 8,394,098 B2 | 3/2013 | Orbay et al. |
| 8,394,130 B2 | 3/2013 | Orbay et al. |
| 8,398,685 B2 | 3/2013 | McGarity et al. |
| 8,403,966 B2 | 3/2013 | Ralph et al. |
| 8,419,775 B2 | 4/2013 | Orbay et al. |
| 8,435,272 B2 | 5/2013 | Dougherty et al. |
| 8,439,916 B2 | 5/2013 | Coati et al. |
| 8,439,918 B2 | 5/2013 | Gelfand |
| 8,444,679 B2 | 5/2013 | Ralph et al. |
| 8,449,583 B2 | 5/2013 | Krebs et al. |
| 8,460,293 B2 | 6/2013 | Coati et al. |
| 8,491,593 B2 | 7/2013 | Prien et al. |
| 8,506,608 B2 | 8/2013 | Cerynik et al. |
| 8,512,338 B2 | 8/2013 | Rabiner et al. |
| 8,512,384 B2 | 8/2013 | Beutter et al. |
| 8,512,385 B2 | 8/2013 | White et al. |
| 8,518,090 B2 | 8/2013 | Huebner et al. |
| 8,523,862 B2 | 9/2013 | Murashko, Jr. |
| 8,523,919 B2 | 9/2013 | Huebner et al. |
| 8,523,921 B2 | 9/2013 | Horan et al. |
| 8,540,755 B2 | 9/2013 | Whitmore |
| 8,545,499 B2 | 10/2013 | Lozier et al. |
| 8,551,095 B2 | 10/2013 | Fritzinger et al. |
| 8,551,143 B2 | 10/2013 | Norris et al. |
| 8,568,462 B2 | 10/2013 | Sixto, Jr. et al. |
| 8,574,233 B2 | 11/2013 | Rabiner et al. |
| 8,574,268 B2 | 11/2013 | Chan et al. |
| 8,591,512 B2 | 11/2013 | Appenzeller et al. |
| 8,597,334 B2 | 12/2013 | Mocanu |
| 8,603,147 B2 | 12/2013 | Sixto, Jr. et al. |
| 8,608,743 B2 | 12/2013 | Baumgartner et al. |
| 8,617,160 B2 | 12/2013 | Quiney et al. |
| 8,617,224 B2 | 12/2013 | Kozak et al. |
| 8,628,578 B2 | 1/2014 | Miller et al. |
| 8,632,544 B2 | 1/2014 | Haaja et al. |
| 8,632,574 B2 | 1/2014 | Kortenbach et al. |
| 8,641,741 B2 | 2/2014 | Murashko, Jr. |
| 8,641,744 B2 | 2/2014 | Weaver et al. |
| 8,663,224 B2 | 3/2014 | Overes et al. |
| 8,728,082 B2 | 5/2014 | Fritzinger et al. |
| 8,728,126 B2 | 5/2014 | Steffen |
| 8,740,905 B2 | 6/2014 | Price et al. |
| 8,747,442 B2 | 6/2014 | Orbay et al. |
| 8,764,751 B2 | 7/2014 | Orbay et al. |
| 8,764,808 B2 | 7/2014 | Gonzalez-Hernandez |
| 8,777,998 B2 | 7/2014 | Daniels et al. |
| 8,790,376 B2 | 7/2014 | Fritzinger et al. |
| 8,790,377 B2 | 7/2014 | Ralph et al. |
| 8,808,333 B2 | 8/2014 | Kuster et al. |
| 8,808,334 B2 | 8/2014 | Strnad et al. |
| 8,814,867 B2 | 8/2014 | Anderson |
| 8,834,468 B2 | 9/2014 | Justin |
| 8,834,532 B2 | 9/2014 | Velikov et al. |
| 8,834,537 B2 | 9/2014 | Castanada et al. |
| 8,840,612 B2 | 9/2014 | Tontz |
| 8,852,187 B2 | 10/2014 | Pool et al. |
| 8,852,246 B2 | 10/2014 | Hansson |
| 8,852,249 B2 | 10/2014 | Ahrens et al. |
| 8,864,802 B2 | 10/2014 | Schwager et al. |
| 8,870,931 B2 | 10/2014 | Dahners et al. |
| 8,876,821 B2 | 11/2014 | Kinmon |
| 8,876,822 B2 | 11/2014 | Fagan et al. |
| 8,888,825 B2 | 11/2014 | Batsch et al. |
| 8,894,656 B2 | 11/2014 | Levy et al. |
| 8,906,022 B2 | 12/2014 | Krinke et al. |
| 8,906,030 B2 | 12/2014 | Rabiner et al. |
| 8,906,076 B2 | 12/2014 | Mocanu et al. |
| 8,911,482 B2 | 12/2014 | Lee et al. |
| 8,915,917 B2 | 12/2014 | Doherty et al. |
| 8,926,675 B2 | 1/2015 | Leung et al. |
| 8,936,644 B2 | 1/2015 | Rabiner et al. |
| 8,940,026 B2 | 1/2015 | Hilse et al. |
| 8,940,028 B2 | 1/2015 | Austin et al. |
| 8,940,029 B2 | 1/2015 | Leung et al. |
| 8,951,291 B2 | 2/2015 | Impellizzeri |
| 8,968,368 B2 | 3/2015 | Tepic |
| 9,011,457 B2 | 4/2015 | Grady, Jr. et al. |
| 9,023,052 B2 | 5/2015 | Lietz et al. |
| 9,050,151 B2 | 6/2015 | Schilter |
| 9,072,555 B2 | 7/2015 | Michel |
| 9,072,557 B2 | 7/2015 | Fierlbeck et al. |
| 9,107,678 B2 | 8/2015 | Murner et al. |
| 9,107,711 B2 | 8/2015 | Hainard |
| 9,107,713 B2 | 8/2015 | Horan et al. |
| 9,107,718 B2 | 8/2015 | Isch |
| 9,113,970 B2 | 8/2015 | Lewis et al. |
| 9,149,310 B2 | 10/2015 | Fritzinger et al. |
| 9,161,791 B2 | 10/2015 | Frigg |
| 9,161,795 B2 | 10/2015 | Chasbrummel et al. |
| 9,168,075 B2 | 10/2015 | Dell'Oca |
| 9,179,950 B2 | 11/2015 | Zajac et al. |
| 9,179,956 B2 | 11/2015 | Cerynik et al. |
| 9,180,020 B2 | 11/2015 | Gause et al. |
| 9,211,151 B2 | 12/2015 | Weaver et al. |
| 9,259,217 B2 | 2/2016 | Fritzinger et al. |
| 9,259,255 B2 | 2/2016 | Lewis et al. |
| 9,271,769 B2 | 3/2016 | Batsch et al. |
| 9,283,010 B2 | 3/2016 | Medoff et al. |
| 9,295,506 B2 | 3/2016 | Raven, III et al. |
| 9,314,284 B2 | 4/2016 | Chan et al. |
| 9,320,554 B2 | 4/2016 | Greenberg et al. |
| 9,322,562 B2 | 4/2016 | Takayama et al. |
| 9,370,388 B2 | 6/2016 | Globerman et al. |
| D765,851 S | 9/2016 | Early et al. |
| 9,433,407 B2 | 9/2016 | Fritzinger et al. |
| 9,433,452 B2 | 9/2016 | Weiner et al. |
| 9,468,479 B2 | 10/2016 | Marotta et al. |
| 9,480,512 B2 | 11/2016 | Orbay |
| 9,486,262 B2 | 11/2016 | Andermahr et al. |
| 9,492,213 B2 | 11/2016 | Orbay |
| 9,510,878 B2 | 12/2016 | Nanavati et al. |
| 9,510,880 B2 | 12/2016 | Terrill et al. |
| 9,526,543 B2 | 12/2016 | Castaneda et al. |
| 9,545,277 B2 | 1/2017 | Wolf et al. |
| 9,549,819 B1 | 1/2017 | Bravo et al. |
| 9,566,097 B2 | 2/2017 | Fierlbeck et al. |
| 9,579,133 B2 | 2/2017 | Guthlein |
| 9,622,799 B2 | 4/2017 | Orbay et al. |
| 9,636,157 B2 | 5/2017 | Medoff |
| 9,649,141 B2 | 5/2017 | Raven, III et al. |
| 9,668,794 B2 | 6/2017 | Kuster et al. |
| 9,801,670 B2 | 10/2017 | Hashmi et al. |
| 9,814,504 B2 | 11/2017 | Ducharme et al. |
| 2002/0045901 A1 | 4/2002 | Wagner et al. |
| 2004/0097937 A1 | 5/2004 | Pike et al. |

(56) References Cited

U.S. PATENT DOCUMENTS

| | | |
|---|---|---|
| 2004/0133204 A1* | 7/2004 | Davies .............. A61B 17/7266 606/63 |
| 2005/0107796 A1 | 5/2005 | Gerlach et al. |
| 2005/0131413 A1 | 6/2005 | O'Driscoll et al. |
| 2005/0187551 A1 | 8/2005 | Orbay et al. |
| 2005/0187555 A1 | 8/2005 | Biedermann et al. |
| 2006/0036248 A1* | 2/2006 | Ferrante ............. A61B 17/7225 606/64 |
| 2006/0149265 A1 | 7/2006 | James et al. |
| 2006/0229617 A1 | 10/2006 | Meller et al. |
| 2006/0241607 A1 | 10/2006 | Myerson et al. |
| 2006/0264950 A1* | 11/2006 | Nelson .............. A61B 17/7208 606/916 |
| 2007/0173840 A1 | 7/2007 | Huebner |
| 2007/0270849 A1 | 11/2007 | Orbay et al. |
| 2007/0288022 A1 | 12/2007 | Lutz |
| 2008/0021477 A1 | 1/2008 | Strnad et al. |
| 2008/0234749 A1 | 9/2008 | Forstein |
| 2008/0275510 A1 | 11/2008 | Schonhardt et al. |
| 2008/0306550 A1 | 12/2008 | Matityahu |
| 2009/0024172 A1 | 1/2009 | Pizzicara |
| 2009/0024173 A1 | 1/2009 | Reis, Jr. |
| 2009/0118773 A1 | 5/2009 | James et al. |
| 2009/0125028 A1 | 5/2009 | Tiesen et al. |
| 2009/0198285 A1 | 8/2009 | Raven, III |
| 2009/0228010 A1 | 9/2009 | Gonzalez-Hernandez et al. |
| 2009/0228047 A1 | 9/2009 | Derouet et al. |
| 2009/0248084 A1 | 10/2009 | Hintermann |
| 2009/0281543 A1 | 11/2009 | Orbay et al. |
| 2009/0299369 A1 | 12/2009 | Orbay et al. |
| 2009/0312760 A1 | 12/2009 | Forstein et al. |
| 2010/0023012 A1 | 1/2010 | Voor |
| 2010/0057086 A1 | 3/2010 | Price et al. |
| 2010/0114097 A1 | 5/2010 | Siravo et al. |
| 2010/0121326 A1 | 5/2010 | Woll et al. |
| 2010/0274247 A1 | 10/2010 | Grady, Jr. et al. |
| 2011/0106086 A1 | 5/2011 | Laird |
| 2011/0196371 A1 | 8/2011 | Forsell |
| 2011/0218580 A1 | 9/2011 | Schwager et al. |
| 2012/0010667 A1 | 1/2012 | Eglseder |
| 2012/0059424 A1 | 3/2012 | Epperly et al. |
| 2012/0165819 A1 | 6/2012 | Guichet |
| 2012/0203227 A1 | 8/2012 | Martin |
| 2012/0232599 A1 | 9/2012 | Schoenly et al. |
| 2012/0323284 A1 | 12/2012 | Baker et al. |
| 2013/0018426 A1 | 1/2013 | Tsai et al. |
| 2013/0046347 A1 | 2/2013 | Cheng et al. |
| 2013/0060291 A1 | 3/2013 | Petersheim |
| 2013/0072932 A1 | 3/2013 | Stauch |
| 2013/0090655 A1 | 4/2013 | Tontz |
| 2013/0123841 A1 | 5/2013 | Lyon |
| 2013/0123857 A1 | 5/2013 | Biedermann et al. |
| 2013/0138156 A1 | 5/2013 | Derouet |
| 2013/0150851 A1 | 6/2013 | Nardini et al. |
| 2013/0150902 A1 | 6/2013 | Leite |
| 2013/0165981 A1 | 6/2013 | Clasbrummet et al. |
| 2013/0211463 A1 | 8/2013 | Mizuno et al. |
| 2013/0253661 A1 | 9/2013 | D'Agostino et al. |
| 2013/0289630 A1 | 10/2013 | Fritzinger |
| 2013/0325008 A1 | 12/2013 | Kuxhaus et al. |
| 2014/0005728 A1 | 1/2014 | Koay et al. |
| 2014/0018862 A1 | 1/2014 | Koay et al. |
| 2014/0031879 A1 | 1/2014 | Sixto, Jr. et al. |
| 2014/0066998 A1 | 3/2014 | Martin |
| 2014/0094856 A1 | 4/2014 | Sinha |
| 2014/0114368 A1 | 4/2014 | Lin et al. |
| 2014/0121710 A1 | 5/2014 | Weaver et al. |
| 2014/0135769 A1 | 5/2014 | Ziran |
| 2014/0163453 A1 | 6/2014 | Rabiner et al. |
| 2014/0180345 A1 | 6/2014 | Chan et al. |
| 2014/0207138 A1 | 7/2014 | Justin |
| 2014/0222094 A1 | 8/2014 | Militz et al. |
| 2014/0277178 A1 | 9/2014 | O'Kane et al. |
| 2014/0277181 A1 | 9/2014 | Garlock |
| 2014/0316473 A1 | 10/2014 | Pfeffer et al. |
| 2014/0324047 A1 | 10/2014 | Zahrly et al. |
| 2014/0330320 A1 | 11/2014 | Wolter |
| 2014/0358144 A1 | 12/2014 | Kuiken |
| 2014/0378975 A1 | 12/2014 | Castaneda et al. |
| 2015/0032109 A1 | 1/2015 | Pool et al. |
| 2015/0051650 A1 | 2/2015 | Verstreken et al. |
| 2015/0051651 A1 | 2/2015 | Terrill et al. |
| 2015/0073486 A1 | 3/2015 | Marotta et al. |
| 2015/0105829 A1 | 4/2015 | Laird |
| 2015/0112355 A1 | 4/2015 | Dahners et al. |
| 2015/0134011 A1 | 5/2015 | Medoff |
| 2015/0142065 A1 | 5/2015 | Schonhardt et al. |
| 2015/0190185 A1 | 7/2015 | Koay et al. |
| 2015/0209091 A1 | 7/2015 | Sixto, Jr. et al. |
| 2015/0216571 A1 | 8/2015 | Impellizzeri |
| 2015/0223852 A1 | 8/2015 | Lietz et al. |
| 2015/0272638 A1 | 10/2015 | Langford |
| 2015/0282851 A1 | 10/2015 | Michel |
| 2015/0313653 A1 | 11/2015 | Ponce et al. |
| 2015/0313654 A1 | 11/2015 | Horan et al. |
| 2015/0327898 A1 | 11/2015 | Martin |
| 2015/0351816 A1 | 12/2015 | Lewis et al. |
| 2015/0374421 A1 | 12/2015 | Rocci et al. |
| 2016/0022336 A1 | 1/2016 | Bateman |
| 2016/0030035 A1 | 2/2016 | Zajac et al. |
| 2016/0045237 A1 | 2/2016 | Cerynik et al. |
| 2016/0045238 A1 | 2/2016 | Bohay et al. |
| 2016/0074081 A1 | 3/2016 | Weaver et al. |
| 2016/0166297 A1 | 6/2016 | Mighell et al. |
| 2016/0166298 A1 | 6/2016 | Mighell et al. |
| 2016/0183990 A1 | 6/2016 | Koizumi et al. |
| 2016/0262814 A1 | 9/2016 | Wainscott |
| 2016/0278828 A1 | 9/2016 | Ragghianti |
| 2016/0310183 A1 | 10/2016 | Shah et al. |
| 2016/0310185 A1 | 10/2016 | Sixto et al. |
| 2016/0324552 A1 | 11/2016 | Baker et al. |
| 2016/0354122 A1 | 12/2016 | Montello et al. |
| 2017/0035478 A1 | 2/2017 | Andermahr et al. |
| 2017/0042592 A1 | 2/2017 | Kim |
| 2017/0042596 A9 | 2/2017 | Mighell et al. |
| 2017/0049493 A1 | 2/2017 | Gauneau et al. |
| 2017/0065312 A1 | 3/2017 | Lauf et al. |
| 2017/0105775 A1 | 4/2017 | Ricker et al. |
| 2017/0215931 A1 | 8/2017 | Cremer et al. |

FOREIGN PATENT DOCUMENTS

| | | |
|---|---|---|
| CN | 202821574 U | 3/2013 |
| CN | 202821575 U | 3/2013 |
| CN | 203506858 U | 4/2014 |
| CN | 203815563 U | 9/2014 |
| CN | 105982727 A | 10/2016 |
| DE | 2305442 | 8/1974 |
| FR | 2846870 A1 | 5/2004 |
| FR | 2928259 A1 | 9/2009 |
| JP | 2003210478 A | 7/2003 |
| SU | 902735 | 2/1982 |
| TW | 201316942 A | 5/2013 |
| WO | 2016079504 A1 | 5/2016 |

* cited by examiner

# EXPANDALBE INTRAMEDULLARY SYSTEMS AND METHODS OF USING THE SAME

CROSS REFERENCE TO RELATED APPLICATIONS

The present application is a continuation application of U.S. patent application Ser. No. 14/946,939 filed on Nov. 20, 2015, which is incorporated in its entirety herein.

FIELD OF THE INVENTION

The present disclosure relates generally to expandable intramedullary systems and methods for treating long bones, and more particularly to expandable intramedullary nails and anchors that are adapted to prevent movement (e.g., axial rotation and/or translation) of the nail when implanted in an intramedullary canal of a long bone.

BACKGROUND

Long bones may generally refer to a femur, tibia, humerus, or other long bone of a mammal, such as a human. For the purpose of clarity, the femur bone will be discussed herein as an example of the deficiencies associated with traditional intramedullary nails.

As is known in the art, the thighbone of a person is called a femur and the long, straight part of the femur is called the femoral shaft, the proximal end is known as the hip. When there is a break anywhere along the length of the femoral shaft, it is called a femoral shaft fracture. Fractures near the hip are known as hip fractures. There are many types of fractures, such as transverse fractures, oblique fractures, spiral fractures, commonuted fractures, etc., each of which could be caused by high-energy collisions or low-energy geriatric fragility fractures.

Intramedullary nailing is one type of operation that is able to treat these femoral fractures. This operation typically involves drilling a hole at one end of the femur away from the femoral fracture. Once the hole has been drilled into the femur, a metal nail having a distal portion and a proximal portion is inserted into the hole, with the distal portion of the nail passing the fracture. To prevent movement of the nail, locking of the nail is required.

Historically, this has been accomplished by inserting one or more bicortical bone screws through holes arranged at the distal portion, proximal portion, or along a length of the implanted nail. One disadvantage in this technique is that additional incisions are required to be made on the patient to insert the bicortical bone screws through the holes of the implanted nail to achieve the desired locking. This technique increases the patient's chances of being exposed to infection and, moreover, moves away from the desire for minimally invasive operations. This technique also makes aiming difficult, can be time consuming, and may be error prone.

Therefore, there exists a need to provide an intramedullary nail that can cure some or many of the deficiencies of more traditional systems.

SUMMARY

To meet this and other needs, expandable intramedullary systems are provided that have integrated distal locking and/or proximal locking, which are designed to prevent rotation and/or axial movement of the intramedullary nail once implanted. In particular, the intramedullary system may include an expandable intramedullary nail or rod and/or one or more expandable anchors. The intramedullary system may include one or more integrated expansion mechanisms configured to secure the intramedullary nail in a long bone.

One of the expansion mechanisms may include an expandable distal portion in order to achieve distal locking of the intramedullary nail. Another expansion mechanism may include an expandable proximal anchor configured to secure the proximal portion of the intramedullary nail. These expandable mechanisms are able to cure certain deficiencies of traditional intramedullary nails by providing an expandable intramedullary nail and/or expandable anchor. In particular, the expandable intramedullary nail and/or expandable anchor may be inserted in a contracted state requiring smaller access to the surgical location while also achieving enhanced locking once expanded. In addition, the expandable intramedullary nail may not require additional incisions being made on the patient to achieve distal locking and the expandable anchor may provide for more robust proximal locking of the intramedullary nail. The expandable intramedullary nail also provides one or more mechanisms that enable a surgeon to perform distal locking of the intramedullary nail before or after proximal locking has taken place.

According to one embodiment, the intramedullary system includes an intramedullary nail configured to extend into an intramedullary canal of a long bone and at least one anchor configured to extend at an angle transverse to the intramedullary nail. The intramedullary nail and/or the anchor may be provided with expansion mechanisms having contracted and expanded positions.

In an illustrative embodiment, the intramedullary system includes an expandable intramedullary nail and at least one expandable anchor. The expandable intramedullary nail is configured to extend through an intramedullary canal of a long bone. The intramedullary nail comprises an elongate nail body having a proximal portion and a distal portion. An elongate adjustment rod extends through the nail body. An actuation member is configured to move the adjustment rod longitudinally through the nail body. The proximal portion has an opening extending therethrough, and the distal portion has one or more expandable fixation members disposed in the nail body in a contracted position. Upon rotation of the actuation member, the adjustment rod linearly translates through the nail body, and the one or more fixation members radially extend from the intramedullary nail to an expanded position to securely anchor the distal portion of intramedullary nail in the intramedullary canal. The expandable proximal anchor is positioned through the opening and transverse to the intramedullary nail. The proximal anchor has a cannulated elongate body, an actuation mechanism extending longitudinally through the elongate body, and at least one expandable securing member engaged with the actuation mechanism. The actuation mechanism is configured to deploy the at least one securing member from the elongate body upon linear movement of the actuation mechanism.

In an illustrative embodiment, the expandable intramedullary nail comprises a longitudinal nail body adapted to be inserted into an intramedullary canal of a long bone, such as a femur. The nail body has a laterally angled through-hole adapted to receive an anchor, such as a femoral neck nail, so as to provide proximal locking of the intramedullary nail to the femur bone. The intramedullary nail further comprises an adjustment rod having a distal portion and a proximal portion. The proximal portion is arranged with a lateral opening through which the proximal anchor is received.

Because the longitudinal length of the lateral opening is longer than the diameter of the received proximal anchor, the adjustment rod is able to move longitudinally within the nail body. The longitudinal movement of the adjustment rod radially deploys one or more fixation members disposed within the nail body. The fixation members engage the inner surface of the intramedullary canal (e.g., cortical bone) to prevent axial rotation and translation of the intramedullary nail, thereby providing distal locking of the intramedullary nail to the femur bone without addition incisions.

In another illustrative embodiment, the expandable anchor includes a cannulated elongate anchor body having a proximal portion and a distal portion, an elongate actuation mechanism extending longitudinally through the anchor body, and configured to move longitudinally through the anchor body, and one or more expandable securing members engaged with the actuation mechanism and disposed in the anchor body in a contracted position. Upon linear translation of the actuation mechanism toward the distal portion of the anchor body, the one or more securing members radially extend from the anchor body to an expanded position to securely anchor the distal portion of anchor body.

In yet another illustrative embodiment, a method of securing a long bone may include inserting an expandable intramedullary nail into an intramedullary canal of a long bone and inserting a proximal anchor through the intramedullary nail. The method may include deploying one or more expandable fixation members from the intramedullary nail by rotating the actuation member and thereby moving the adjustment rod longitudinally through the nail body, wherein the fixation members radially extend from the intramedullary nail to an expanded position to securely anchor the distal portion of intramedullary nail in the intramedullary canal. If expandable, the method may also include deploying one or more expandable securing members from the elongate body of the anchor by linear movement of the actuation mechanism, wherein the securing members radially extend from the anchor to an expanded position to securely anchor the proximal portion of intramedullary nail in the intramedullary canal.

These advantages of the present invention will be apparent from the following disclosure and the appended claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figure 1:
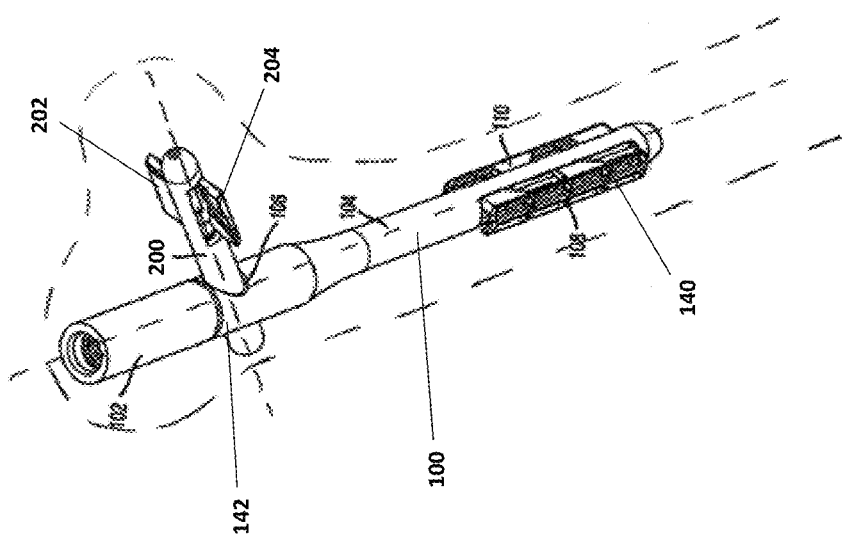
FIG. 1 is a perspective view of an expandable intramedullary system, in a deployed state, positioned within a long bone according to one embodiment.

Embodiments of the disclosure are generally directed to systems, devices, and methods for stabilizing fractures or the like of long bones and other hollow bones. The intramedullary system may include an intramedullary nail configured to extend into an intramedullary canal of a long bone and at least one anchor configured to extend at an angle transverse to the intramedullary nail. The intramedullary system may include one or more integrated expansion mechanisms configured to secure the intramedullary nail in the bone. In particular, the intramedullary nail may include an expandable distal portion in order to achieve distal locking of the intramedullary nail. The anchor may be in the form of a proximal anchor configured to extend into a neck portion of the long bone. The anchor may include an expandable proximal anchor configured to secure the proximal portion of the intramedullary nail. The expandable intramedullary nail and expandable anchor may be used together in combination or each may be used separately with traditional intramedullary nails or anchors, respectively.

It will be appreciated by those of skill in the art that a long bone may include any bone that is longer than it is wide. Examples of long bones may include, but are not limited to the femur, tibia, fibula, humerus, radius, ulna, and phalanges. The description herein generally refers to treatment of a femur, but the systems, devices, and methods may be equally applied to any other long or hollow bone structure. It is also contemplated that the expansion mechanisms described herein may have applicability in other areas including those outside of long bone applications.

The embodiments of the disclosure and the various features and advantageous details thereof are explained more fully with reference to the non-limiting embodiments and examples that are described and/or illustrated in the accompanying drawings and detailed in the following description. The features of one embodiment may be employed with other embodiments as the skilled artisan would recognize, even if not explicitly stated herein. Descriptions of well-known components and processing techniques may be omitted so as to not unnecessarily obscure the embodiments of the disclosure. The examples used herein are intended merely to facilitate an understanding of ways in which the disclosure may be practiced and to further enable those of skill in the art to practice the embodiments of the disclosure. Accordingly, the examples and embodiments herein should not be construed as limiting the scope of the disclosure, which is defined solely by the appended claims and applicable law. Moreover, it is noted that like reference numerals represent similar features and structures throughout the several views of the drawings.

Intramedullary System

Referring now to FIG. 1, the intramedullary system 10 may include an intramedullary nail 100 in combination with one or more anchors 200. The intramedullary system 10 may include an intramedullary nail 100 configured to extend into an intramedullary canal or positioned into the medullary cavity of a bone. Although described as a nail, it will be appreciated that the intramedullary nail 100, also known as an IM nail, may be in the form of a rod, shaft, elongate member, or the like. The anchor 200 may be configured to extend at an angle transverse to the intramedullary nail 100. As will again be appreciated, the anchor 200 may be in the form of a screw, nail, rod, shaft, elongate member, or the like. Depending on the position, number, and type of anchors, the anchor 200 may be positioned at any suitable angle or orientation relative to the intramedullary nail 100. When positioned at a proximal location of the intramedullary nail 100 to provide for proximal fixation of the intramedullary nail 100, the anchor 200 may be positioned at an angle such that the distal end of the anchor 200 extends upwards into the neck portion of the long bone (e.g., the femoral neck of a femur). One of the significant advantages of the intramedullary system 10 over other systems and methods of fixation is the intramedullary system 10 shares the load with the bone, rather that entirely supporting the bone. Due to this load sharing, patients may be able to use the extremity more quickly. In addition, with the expandable components described herein, the patient may require smaller and/or fewer incisions (e.g., those typically needed for the placement of larger fixation devices and/or multiple fixation points) leading to improved patient outcomes and healing times.

The intramedullary system 10 may include one or more integrated expansion mechanisms configured to secure the intramedullary nail 100 and/or anchor 200 in the bone once expanded. In addition, when in a contracted position, the integrated expansion mechanism allows for a smaller surgical access window to insert the device. In particular, the intramedullary nail 100 may include an expandable distal portion 140 in order to achieve distal locking of the intramedullary nail 100. The proximal portion 142 of the intramedullary nail 100 may be secured with one or more traditional bone nails, screws, or the like (not shown). In the alternative, the proximal portion of the intramedullary nail 100 may be secured with the expandable anchor 200 configured to extend into the neck portion of the long bone (e.g., the femoral neck of the femur), thereby securing the proximal portion 142 of the intramedullary nail 100 once expanded. The expandable proximal anchor 200 can also be used with a traditional, non-expandable intramedullary nail or rod (not shown). Although one anchor 200 is exemplified herein, it will be appreciated that additional anchors including traditional anchors and/or expandable anchors may be used in the intramedullary system 10. In addition, although one expansion mechanism is described with respect to the intramedullary nail 100 and another expansion mechanism is described further with respect to the proximal anchor 200, it will be appreciated that the expansions mechanisms may be switched or modified in order to achieve the desired fixation in the bone.

Expandable Intramedullary Nail

Figure 2:
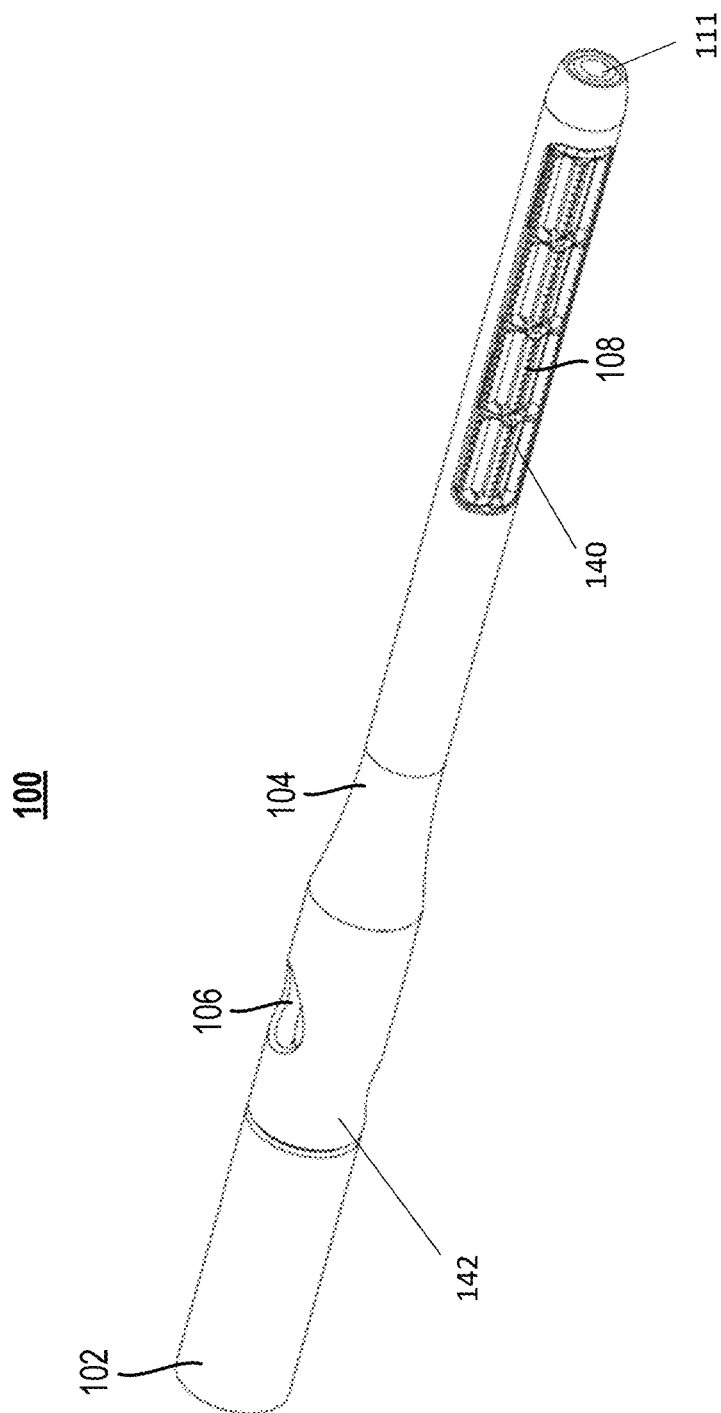
FIG. 2 is a perspective view of the intramedullary nail in an un-deployed state according to an illustrative embodiment.
Figure 3:
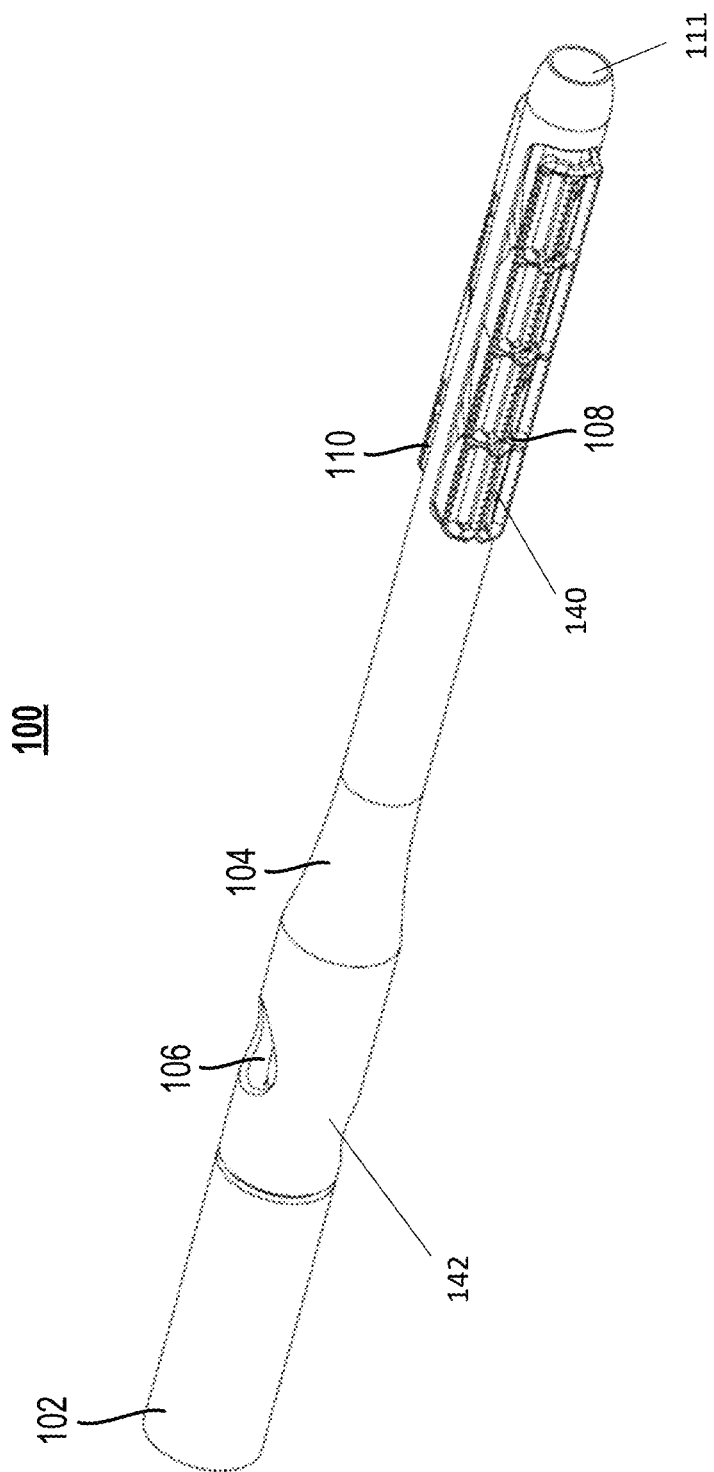
FIG. 3 is a perspective view of the intramedullary nail of FIG. 2 in a deployed state according to an illustrative embodiment.

According to one embodiment, the intramedullary nail 100 includes an expandable distal portion 140 in order to achieve distal locking of the intramedullary nail 100. The expandable intramedullary nail 100 is configured to be inserted into the intramedullary canal of a long bone while in a contracted or un-deployed state. FIG. 2 is a perspective view of one version of the intramedullary nail 100 in an un-deployed state. After the intramedullary nail 100 has been positioned in the long bone, the intramedullary nail 100 can be actuated, for example, using mechanical actuation, to expand or deploy the expandable distal portion 140 to an expanded or deployed state. FIG. 3 is a perspective view of intramedullary nail 100 in a deployed state. Unlike other devices which may use an inflatable device or cavity, for example, filled with bone cement or the like in order to expand a portion of the intramedullary nail, the expandable intramedullary nail 100 relies on one or more mechanically actuated mechanisms to expand the expandable distal portion 140.

In the embodiment shown in FIGS. 2 and 3, expandable distal portion 140 of the intramedullary nail 100 includes one or more expandable or deployable fixation members 108, 110. In particular, as shown, the intramedullary nail 100 includes a cannulated elongate sleeve 102, a cannulated longitudinal nail body 104 having at least one lateral through-hole 106, a first expandable fixation member 108, and a second expandable fixation member 110. Although two fixation members 108, 110 are shown, it is envisioned that any suitable number, size, and type of fixation members may be selected to obtain the desired fixation and press-fit type anchoring when expanded in the intramedullary canal. In particular, the expandable distal portion 140 may include one or more plates, projections, extensions, spikes, teeth, pointed members, or the like configured to emerge from within the intramedullary nail body 104. Moreover, the fixation members 108, 110 may be generally flat, contoured, provided with surface roughening or teeth, or have any characteristics to enhance locking of the distal portion 140 of the intramedullary nail 100 when expanded.

In addition, unlike other devices which may use a shape-memory alloy or other shape-memory technique for the fixation members to automatically deploy from the device, the expandable intramedullary nail 100 is configured such that the expandable distal portion 140 radially expands from the nail 100 with continuous and/or discrete adjustments. In other words, the expandable distal portion 140 is uniquely controlled such that the fixation members 108, 110 can be deployed to any desired amount without requiring full deployment. Since the expansion of the intramedullary nail 100 is actuated by a rotational input, the expansion of the intramedullary nail 100 is infinite. In other words, the fixation members 108, 110 can be expanded to an infinite number of heights dependent on the rotational advancement of the actuation member, such as a drive screw 120. Thus, the fixation members 108, 110 can be deployed to the degree necessary to achieve the desired press-type fit in the intramedullary canal without providing too much stress on the bone.

As shown in FIG. 2, the first fixation member 108 is disposed within a distal portion of longitudinal nail body 104. Although not shown in FIG. 2, second fixation member 110 is similarly disposed within nail body 104. In this embodiment, the first and second fixation members 108, 110 have a plate-like or elongated shape. In particular, the first and second fixation members 108, 108 have a length greater than their width. The first and second fixation members 108, 110 have an outer surface that is substantially planar with a slight curve to conform to the circular cross-sectional shape of nail body 104. The planar surfaces of fixation members 108, 110 may be arranged with teeth having a profile that lies substantially on the same plane as the outer surface of nail body 104 when fixation members 108, 110 are disposed within the nail body 104. This allows a surgeon to more easily insert nail 100 into an intramedullary canal of a femur bone.

The first and second fixation members 108, 110 may be positioned at any suitable location along the length of the nail body 104. The nail body 104 may terminate in a tip 111. The tip 111 may be rounded, curved, or substantially blunt, as shown. Preferably, the first and second fixation members 108, 110 are positioned at a distal-most end of the body 104, for example, proximate to the tip 111. It is envisioned, however, that additional fixation members 108, 110 may be provided along the length of the body 104, for example, substantially centrally along the length of the body 104 or closer to the proximal portion 142. Due to the mechanical functionality of the first and second fixation members 108, 110, the overall length of the nail 100 does not change when the fixation members 108, 110 are expanded. In addition, the dimensions of the fixation members 108, 110 do not change or alter when they are expanded (although more of the fixation member 108, 110 protrudes from the body 104 when expanded).

Figure 4:
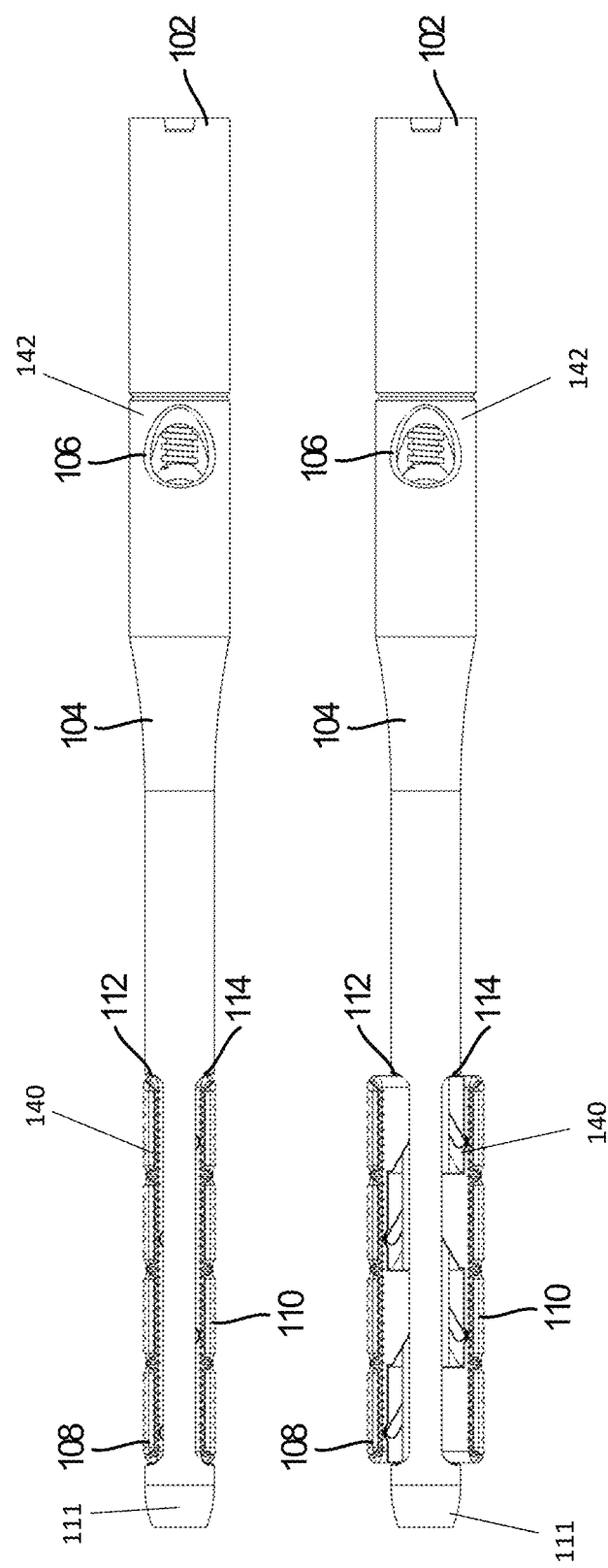
FIG. 4 is a top view of the intramedullary nail of FIGS. 2 and 3 in accordance with an illustrative embodiment.

In one embodiment, the nail body 104 is inserted into the intramedullary canal such that the first and second fixation members 108, 110 pass the femoral fracture of the femur bone. The nail body 104 is inserted in such a way that lateral through-hole 106 of nail body 104 is aligned with the neck of the femur bone. Once the nail body 104 has been situated in the intramedullary canal, a femoral neck nail or proximal anchor 200 is inserted through lateral through-hole 106, which extends into a hole that has been drilled into the femur neck. The femoral neck nail may be locked to nail body 104, thereby providing proximal locking of the nail body 104 to the femur bone. The femoral neck nail can be, for example, and without limitation, a threaded or non-threaded anchor, lag screw, nail, or the like. In other embodiments, discussed in more detail herein, the femoral neck nail is an expandable proximal anchor 200 having one or more securing members 202, 204 that are adapted to radially deploy from the body of the proximal anchor 200 into the femoral neck. In any case, the mechanism for locking proximal anchor 200 to body 104 will be described in more detail below, with respect to FIG. 11. Thereafter, an adjustment rod 116 (shown in FIG. 5) coupled to fixation members 108, 110 is moved, retracted, driven, etc., longitudinally towards the proximal portion 142 of nail body 104. Moving adjustment rod 116 in a longitudinal manner causes the first and second fixation members 108, 110 to be radially deployed from the nail body 104, as shown at the bottom of FIG. 4. In accordance with the illustrative embodiment, first and second fixation members 108, 110 are adapted to be simultaneously deployed from nail body 104 to provide distal locking of the nail body 104 to the shaft of the femur bone. On the other hand, moving adjustment rod 116 longitudinally towards the distal portion of nail body 104 causes the first and second fixation members 108, 110 to be radially retracted into nail body 104, as shown at the top of FIG. 4. Adjustment rod 116 will be described in more detail below, with respect to FIGS. 8-14.

Although intramedullary nail 100 has been generally described above as being used on a femur bone, it will be clear to those skilled in the art, after reading this disclosure, that the intramedullary nail 100 can also be used on any long bone. For example, and without limitation, intramedullary nail 100 can be used on a tibia bone, a humerus bone, etc., without departing from the scope of the present invention.

The intramedullary nail 100 may be preferably made of a biocompatible metal, such as titanium or titanium alloys. However, it will be clear to those skilled in the art, after reading this disclosure, how to make and use alternative embodiments of the invention in which intramedullary nail 100 is made from biocompatible plastics (e.g., polyetheretherketone (PEEK), etc.) or a combination of biocompatible metals and plastics, for example.

FIG. 4 is a top view of intramedullary nail 100 of FIGS. 2 and 3. As shown in the top figure, first and second fixation members 108, 110 are respectively disposed within a first opening 112 and a second opening 114 of nail body 104. The openings 112, 114 can be seen more clearly in FIG. 5. The openings 112, 114 are, for example, and without limitations, slots, recesses, windows, etc., that are sized and shaped to receive fixation members 108, 110, respectively, when they are radially retracted into the nail body 104 by adjustment rod 116. This feature will be discussed in more detail below, with respect to FIGS. 5 and 9-14.

The bottom of FIG. 4 depicts the nail body 104 in a deployed state, in which the first and second fixation members 108, 110 have been extended outside of the openings 112, 114, respectively, by adjustment rod 116. When the fixation members 108, 110 are radially deployed from their respective openings 112, 114, the teeth arranged on the outer planar surfaces of the fixation members 108, 110 engage the inner surface of the intramedullary canal (e.g., cortical bone), thereby providing a press-fit type connection and locking. As will be discussed in more detail below, with respect to FIGS. 11-14, the force in which fixation members 108, 110 engage the inner surface of the intramedullary canal can be adjusted (i.e., increased or decreased) by longitudinally moving adjustment rod 116 further back towards the proximal or distal portions of nail body 104.

Although the first and second fixation members 108, 110 are adapted to simultaneously transition between an un-deployed state and a deployed state, it will be clear to those skilled in the art after reading this disclosure, how to make and use alternative embodiments of the invention in which fixation members 108, 110 are adapted to individually transition between an un-deployed state and a deployed state. In addition, only one fixation member may be deployed or more than two fixation members may be deployed.

Figure 5:
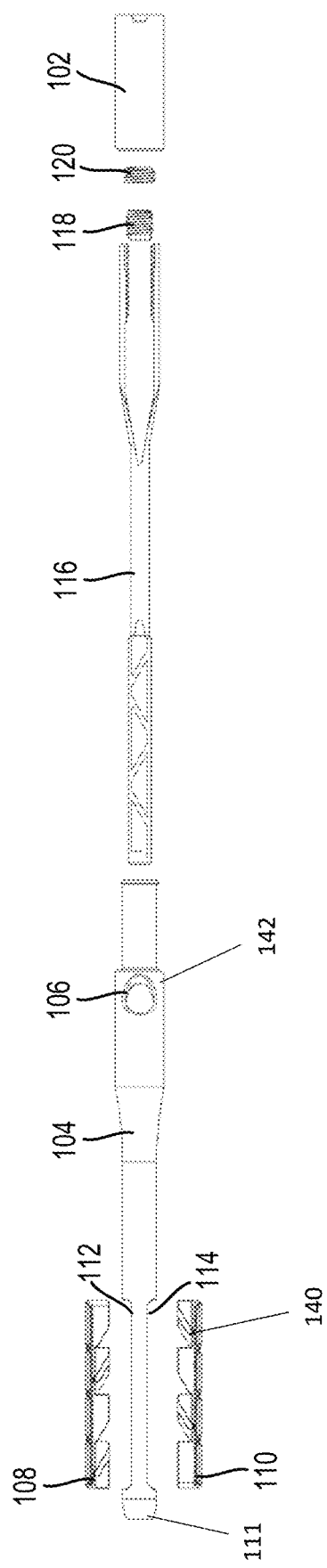
FIG. 5 depicts the elements that form the intramedullary nail in accordance with an illustrative embodiment.

FIG. 5 is an exploded view of the intramedullary nail 100 and the elements that may form the intramedullary nail 100. The intramedullary nail 100 may include an elongate nail body 104, an expandable distal portion 140 (e.g., including one or more fixation members 108, 110), an elongate adjustment rod 116 configured to extend through the nail body 104 and configured to move the expandable distal portion 140, and an actuation mechanism (e.g., one or more screws) configured to move the adjustment rod 116 longitudinally through the nail body 104.

The intramedullary nail 100 may include an elongate nail body 104 having an opening extending longitudinally therethrough. The nail body 100 may be generally cylindrical in shape or may have any other suitable cross-sectional shape. The nail body 100 may have a larger diameter at the proximal portion 142 and may transition to a smaller diameter at the distal end. Arranged at the distal end of nail body 104 are openings 112, 114, each of which is sized and shaped to accommodate the fixation members 108, 110. Specifically, FIG. 5 shows opening 112 sized and shaped to receive the first fixation member 108, while opening 114 is sized and shaped to receive the second fixation member 110. The fixation members 108, 110 are shown in more detail in FIGS. 6 and 7, which will now be discussed. It should be noted at this point of the disclosure that first fixation member 108 and second fixation member 110 are mirror images of each other. For the purpose of clarity, the following discussion of FIGS. 6 and 7 will use the generic word "fixation member 500" to refer to both first and second fixation members 108, 110.

Figure 6:
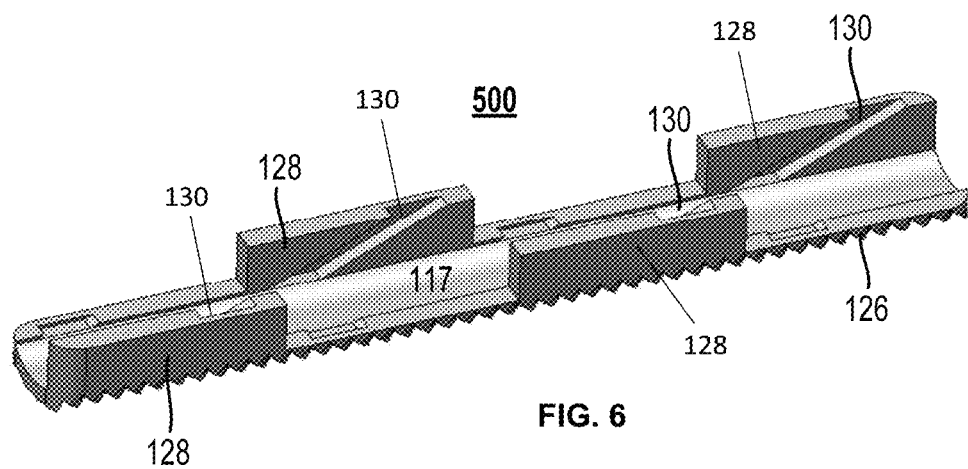
FIG. 6 is a perspective view of the inner surface of a fixation member in accordance with an illustrative embodiment.

FIG. 6 is a perspective view of the inner surface 117 of fixation member 500. The fixation member 500 is preferably made of a biocompatible material, such as a biocompatible metal or biocompatible plastic, such as PEEK. The inner surface 117 of the fixation member 500 has a plurality of spaced apart tabs 128 that extend orthogonally from, and along longitudinal edges of, the inner surface 117. The tabs 128 are spaced apart in such a way to allow tabs of one fixation member interleave, mesh, etc., with tabs of another fixation member after adjustment rod 116 moves longitudinally within nail body 104. As shown, the fixation member 500 may have two spaced apart tabs 128 extending from one edge of the fixation member 500 and two spaced apart tabs 128 extending from the other edge of the fixation member 500. Although two tabs 128 are shown on each edge more or less tabs 128 may be used instead.

Each tab 128 includes at least one ramp or angled surface having a slope. In particular, an inner surface of each tab 128 is arranged with at least one ramp or angled surface having a slope or angle relative to the longitudinal axis of the nail body 104. The ramps or angled surfaces may be in the form of one or more grooves, recesses, projections, protrusions, or the like in the tab 128. The ramp or angled surface may extend from a first end of the tab 128 to a second, opposite end of the tab 128. Although one ramp per tab is exemplified in the figures, it will be appreciated that multiple ramps or angled surfaces may be provided for each tab 128. In addition, it is contemplated that the slope of the ramped surfaces on each tab 128 can be equal or can differ from one another. The ramps can serve to move the fixation members 108, 110 when the adjustment rod 116 is linearly translated between the fixation members 108, 110. In other words, as the adjustment rod 116 moves, the ramped surfaces 134, 136 of the adjustment rod 116 push against the ramped surfaces of the fixation member 108, 110 pushing the fixation members 108, 110 outwardly into the expanded position. It should also be noted that the expansion of the fixation members 108, 110 can be varied based on the differences in the dimensions of the ramped surfaces. The fixation members 108, 110 can be expanded in any of the following ways, for example: straight rise expansion, angled rise expansion, straight rise expansion followed by an angled toggle, or a phase off straight rise.

In one embodiment, each of the tabs 128 has an inner surface that is arranged with an angled surface in the form of a groove 130, with each groove 130 having a predetermined angle relative to a longitudinal axis of nail body 104. The predetermined angle can range, for example, from about 20° to 40° or about 25° to 35° relative to the longitudinal axis of nail body 104. In one embodiment, the predetermined angle can be about 30° relative to the longitudinal axis of nail body 104. It should be noted that changing the orientation of the fixation member 500 shown in FIG. 6 (e.g., a bottom fixation member) to the orientation shown in FIG. 7 (e.g., a top fixation member) would change a 30° angle of the groove to about 120°.

Figure 7:
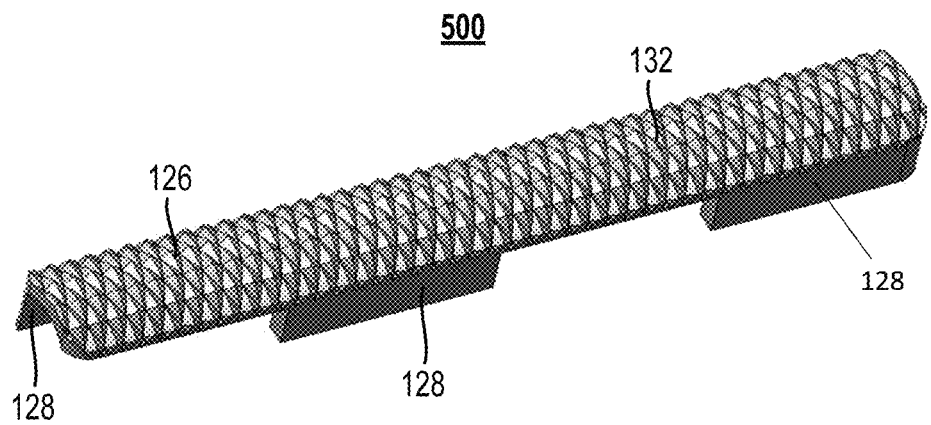
FIG. 7 is a perspective view of the outer surface of the fixation member depicted in FIG. 6.

FIG. 7 is a perspective view of an outer surface 132 of the fixation member 500 depicted in FIG. 6. As shown in this figure, outer surface 132 is substantially planar with a slight curve. This curvature enables the outer surface 132 of the fixation member 500 to conform to the circular shape of nail body 104 when the fixation member 500 is disposed within the nail body 104 and in the contracted position. The planar outer surface 132 of the fixation member 500 may be arranged with a surface roughening, such as teeth 126 or the like having a profile that lies substantially on the same plane as the outer surface of nail body 104 when the fixation member 500 is disposed within nail body 104 in the contracted position. That is, the fixation member 500 is able to retract into the axial profile of the nail body 104 (e.g., ≥09 mm on a 09 mm nail) for insertion into the intramedullary canal of a long bone, such as a femur bone.

The adjustment rod 116 includes at least one ramp or angled surface having a slope sized and configured to mate with the corresponding ramps on the tabs 128 of the fixation members 108, 110. In particular, an outer surface on each side of the adjustment rod 116 is arranged with at least one ramp or angled surface having a slope or angle relative to the longitudinal axis of the adjustment rod 116. The ramps or angled surfaces may be in the form of one or more grooves, recesses, projections, protrusions, or the like in the adjustment rod 116, which are configured to correspond to those of the tab 128.

Figure 8:
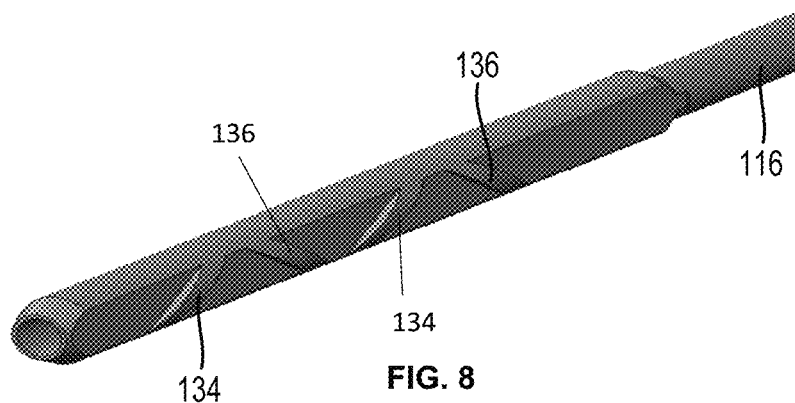
FIG. 8 is a perspective view of the distal portion of the adjustment rod in accordance with an illustrative embodiment.

In one embodiment, FIG. 8 is a perspective view of a distal portion of the adjustment rod 116. The distal portion of the adjustment rod 116 is arranged with a first plurality of angled tongues 134 and a second plurality of angled tongues 136 configured to engage with the corresponding angled grooves 130 of the first and second fixation members 108, 110, respectively. The tongues 134, 136 may be in the form of extensions or protrusions projecting from an outer surface of the adjustment rod 116 or may be formed or defined by triangular cut-outs or recesses in the adjustment rod 116. The adjustment rod 116 may be solid or may be cannulated along its length and may extend generally to the tip 111 of the nail 100, for example, when in the contracted position.

Although the ramps on the adjustment rod 116 exemplified in the figures, it will be appreciated that one or more ramps or angled surfaces may be provided having the same or different orientations. The ramps can serve to move the fixation members 108, 110 when the adjustment rod 116 is linearly translated between the fixation members 108, 110. Thus, as the adjustment rod 116 moves, the ramped surfaces 134, 136 of the adjustment rod 116 push against the ramped surfaces of the fixation member 108, 110 pushing the fixation members 108, 110 outwardly into the expanded position.

By way of example, as best seen in FIGS. 9 and 10, the distal portion of adjustment rod 116 may be arranged with the second plurality of tongues 136 having a predetermined angle which corresponds substantially to the predetermined angle of the grooves 130 in the tabs 128 of the first fixation member 108. In the case where the predetermined angle of the grooves 130 is about 120°, for example, for the top or upper fixation member 108 (e.g., FIG. 7), the tongues 134 have a corresponding angle of about 120°. Similarly, the distal portion of the adjustment rod 116 may be arranged with the first plurality of tongues 134 having a predetermined angle which corresponds substantially to the predetermined angle of the grooves 130 in the tabs 128 of the second fixation member 110. In the case where the predetermined angle of the grooves 130 is about 30°, for example, for the bottom or lower fixation member 110 (e.g., FIG. 6), the tongues 134 have a corresponding angle of about 30°.

The first plurality of tongues 134 are sized and shaped to be received by grooves 130 arranged on tabs 128 of the second fixation member 110 (as shown in FIGS. 9 and 10). The second plurality of tongues 136 are sized and shaped to be received by grooves 130 arranged on tabs 128 of the first fixation member 108 (as shown in FIGS. 9 and 10). Each tongue 134, 136 is adapted 130 to slide along its respective groove 130 to radially retract or deploy the first and second fixation members 108, 110, respectively, from the nail body 104 when the adjustment rod 116 is slid relative to the fixation members 108, 110. In particular, the fixation members 108, 110 can be retracted or deployed as adjustment rod 116 is moved longitudinally within the nail body 104. In particular, as the adjustment rod 116 is translated proximally, the fixation members 108, 110 are configured to extend radially outward into the intramedullary canal. When the adjustment rod is translated distally, the fixation members 108, 110 are configured to retract inward into the body 104 of the intramedullary nail 100. It will be clear to those skilled in the art, after reading this disclosure, how to make and use alternative embodiments of the present invention including those in which tongues 134, 136 are arranged on tabs 128 and grooves 130 are arranged on the adjustment rod 116, instead.

Figure 9A:
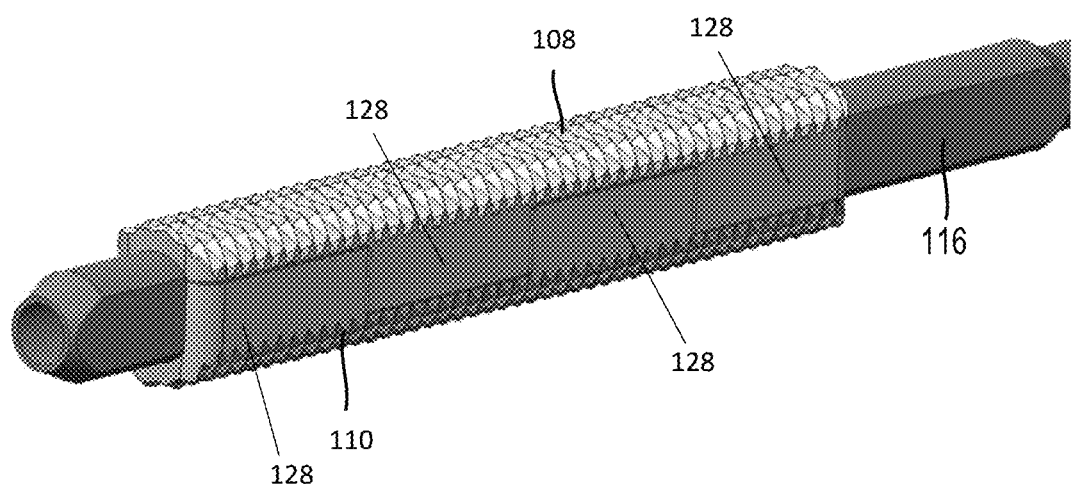
FIG. 9A is a perspective view of one fixation member meshed with another fixation member in accordance with an illustrative embodiment.

FIG. 9A is a perspective view of first fixation member 108 meshed with second fixation member 110 when in an un-deployed or contracted configuration. As shown in the figure, the spaced apart tabs 128 of first fixation member 108 are interleaved or intermeshed with the spaced apart tabs 128 of second fixation member 110. In this configuration, first and second fixation members 108, 110 are disposed within nail body 104 and in their respective openings 112, 114, as shown at the top of FIG. 4. When in the contracted configuration, the tabs 128 are aligned such that there is minimal or no gap between the first and second fixation members 108, 110. Also, the tabs 128 may be configured such that a substantially solid outer wall forms when the nail is in the retracted position such that tissue, etc. does not become trapped in the device when inserted into the intramedullary canal. Although the tabs 128 are depicted as substantially rectangular in shape with a dovetail-like configuration, it is envisioned that other configurations could also provide for a dovetail design (e.g., t-shaped, triangular, curvilinear, or scalloped), thereby allowing the fixation members 108 to mate together when the retracted position.

Figure 9B:
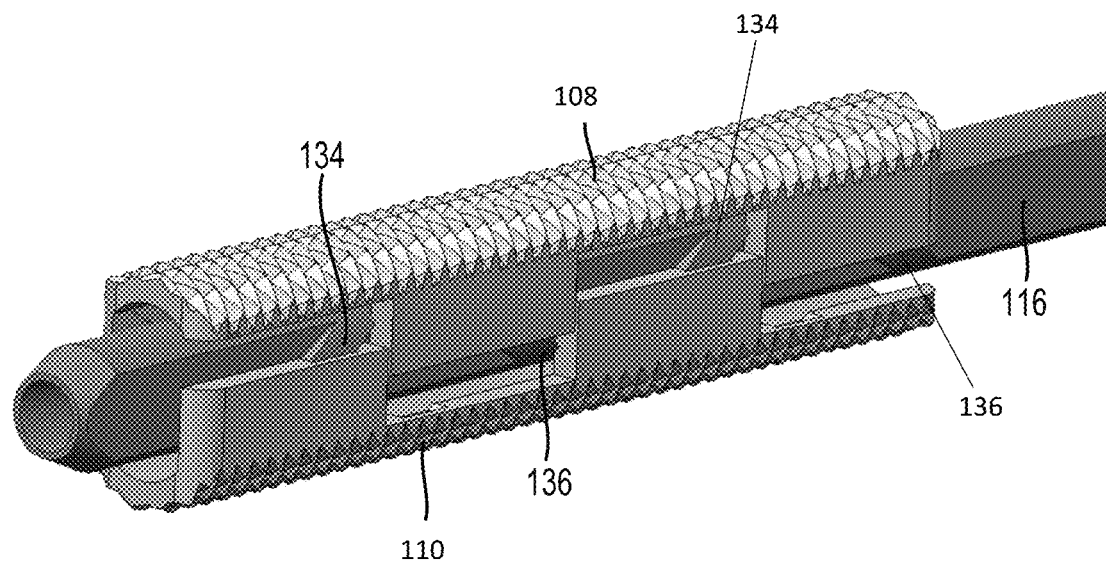
FIG. 9B is a perspective view of two fixation members being radially deployed from intramedullary nail by an adjustment rod in accordance with an illustrative embodiment.

FIG. 9B is a perspective view of the first and second fixation members 108, 110, for example, when radially deployed from the nail body 104 by the adjustment rod 116. As the adjustment rod 116 is moved towards a proximal portion of nail body 104, the first and second fixation members 108, 110 radially extend outside of openings 112, 114, respectively, as shown at the bottom of FIG. 4. Thus, upon the linear movement of the adjustment rod 116, the first and second fixation members 108, 110 discretely and continuously expand outside the nail body 104 to anchor the distal end of the intramedullary nail 100 in the bone.

Figure 10A:
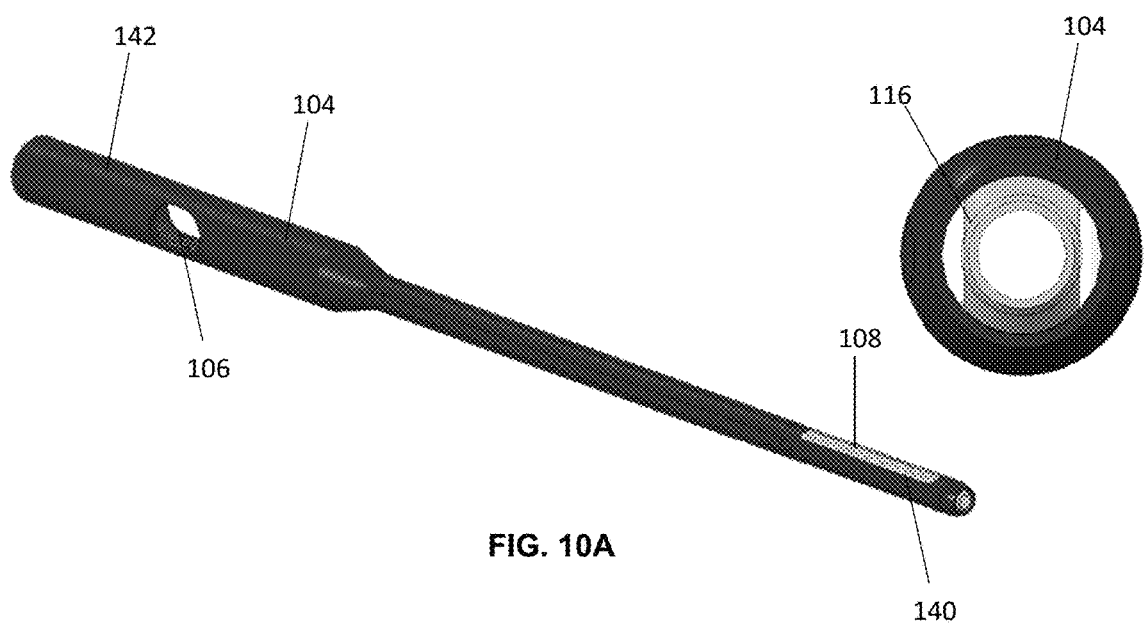
FIG. 10A is a perspective view and a close up front view of the intramedullary nail in an un-deployed state according to an illustrative embodiment.
Figure 10B:
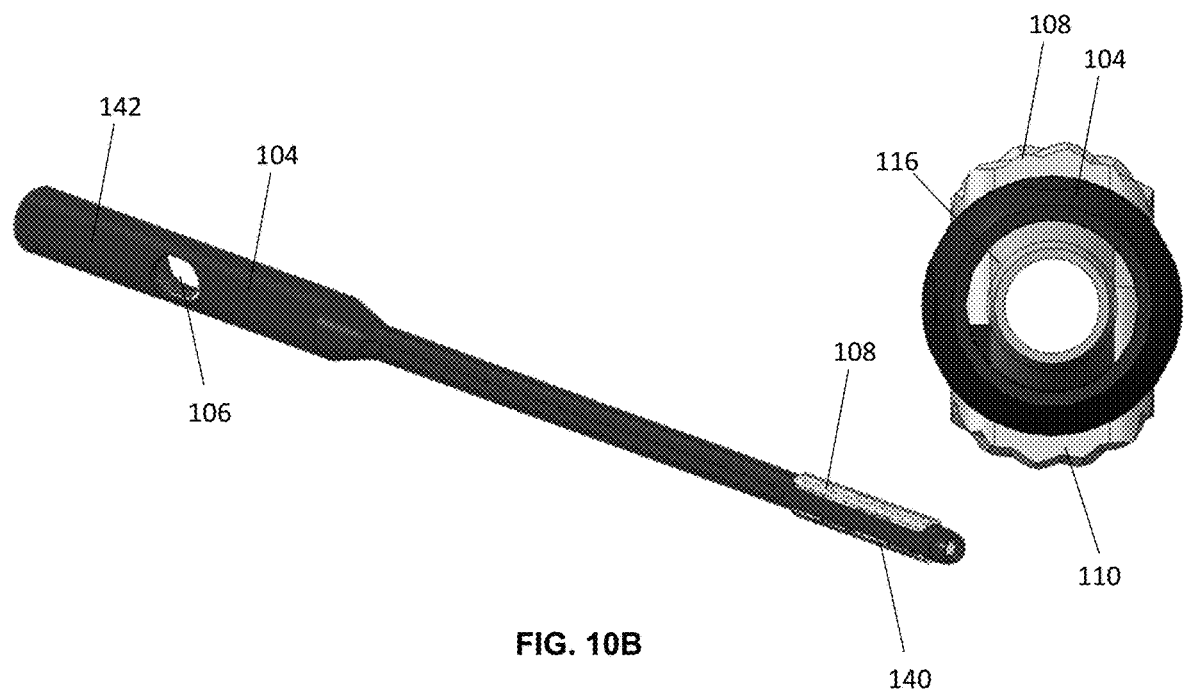
FIG. 10B is a perspective view and a close up front view of the intramedullary nail in a deployed state according to an illustrative embodiment.

FIG. 10A shows a perspective view of the intramedullary nail 100 including a close-up front view with the first and second fixation members 108, 110 in an un-deployed state. As is evident, in the front view, the first and second fixation members 108, 110 are recessed in the nail body 104. FIG. 10B shows a perspective view of the intramedullary nail 100 including a close-up front view with the first and second fixation members 108, 110 in a deployed state. As is evident, in the front view, the first and second fixation members 108, 110 protrude outwardly from the nail body 104.

Figure 11:
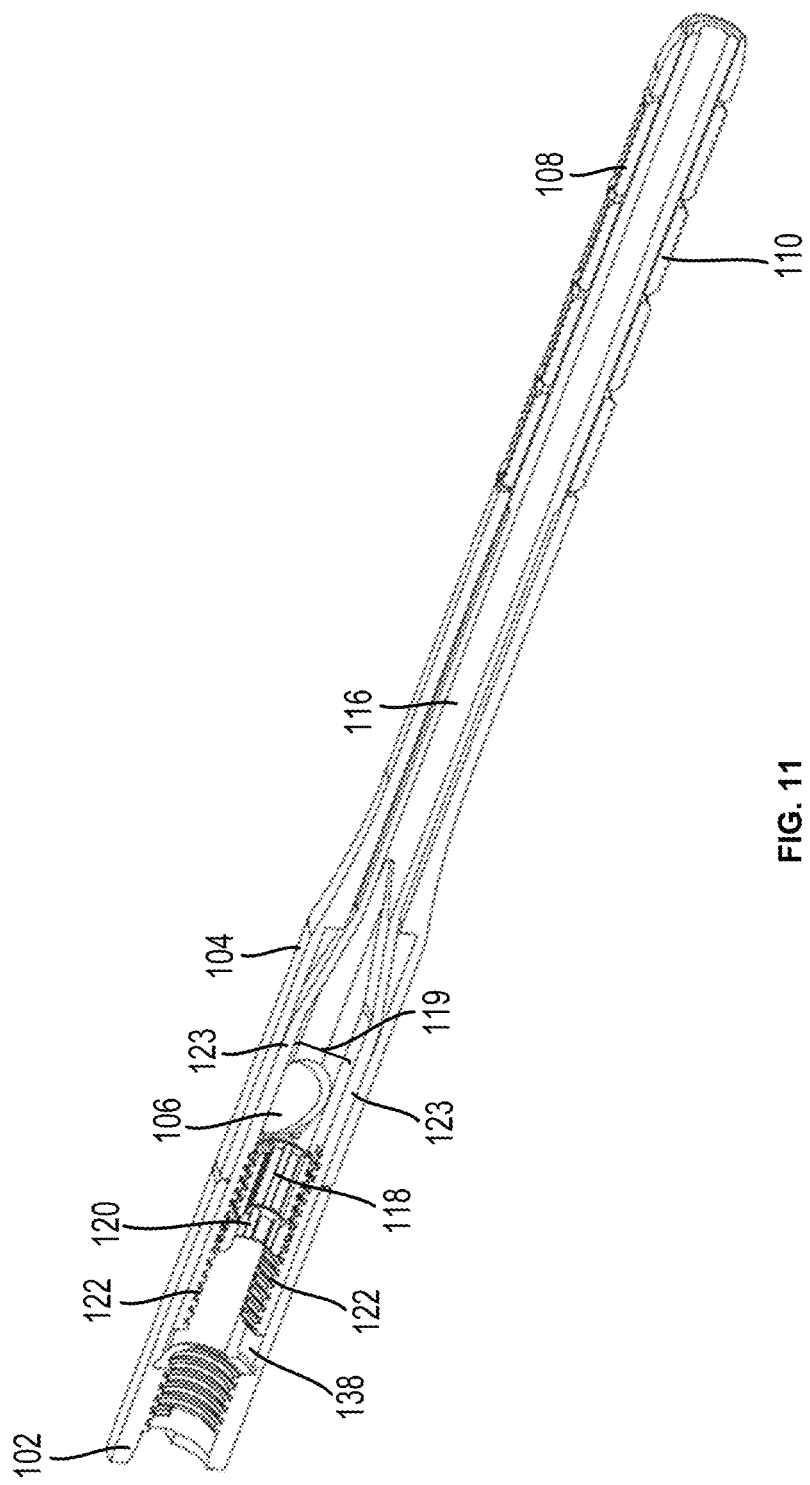
FIG. 11 is a cross-sectional side view of the intramedullary nail of FIG. 2 in the un-deployed state according to an illustrative embodiment.
Figure 12:
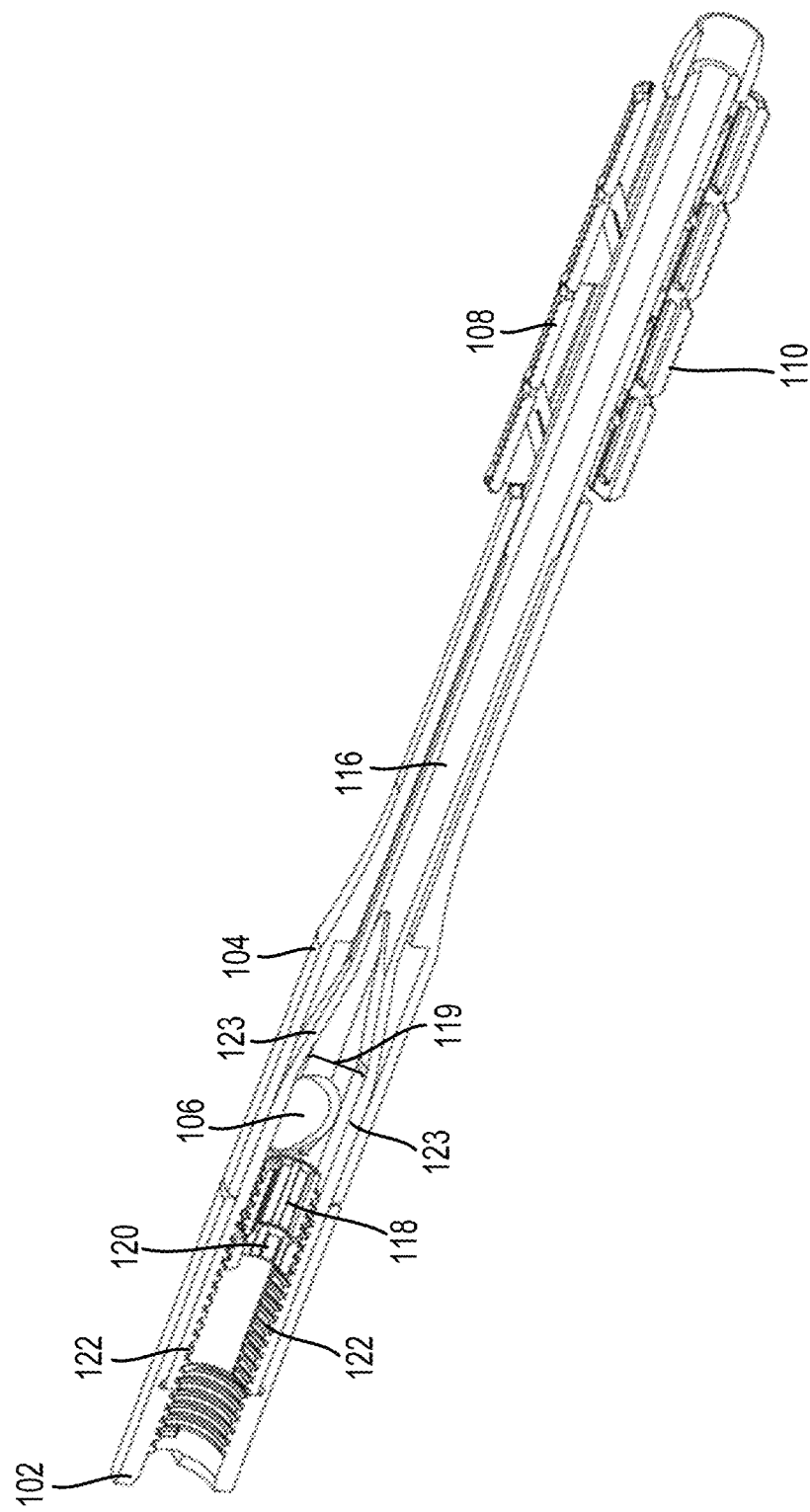
FIG. 12 is a cross-sectional side view of the intramedullary nail of FIG. 3 in the deployed state according to an illustrative embodiment.
Figure 15:
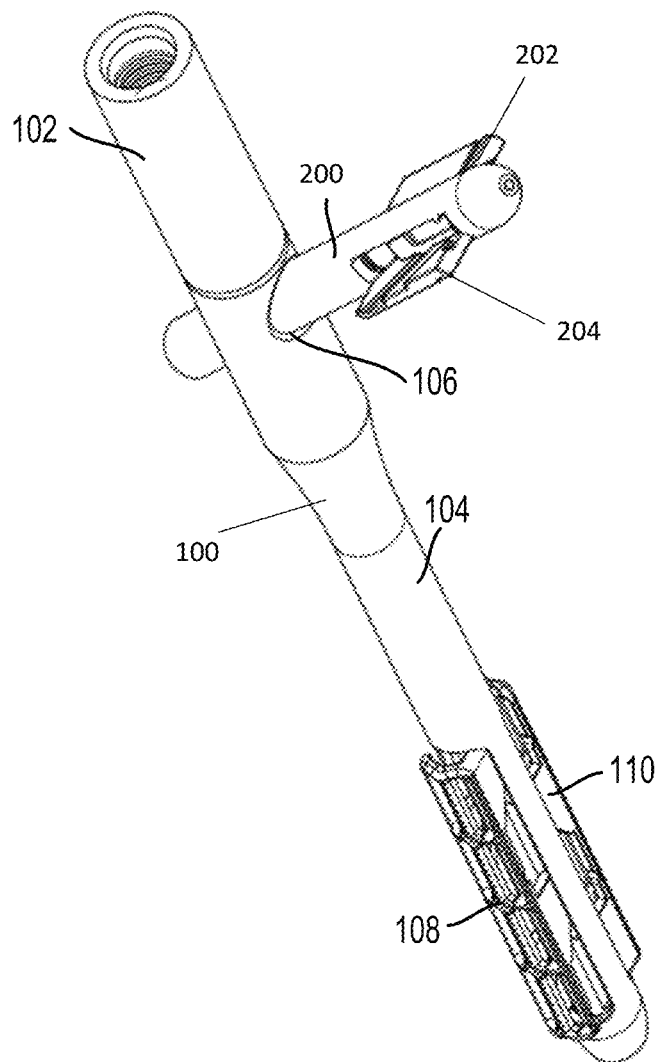
FIG. 15 is a perspective view of a proximal anchor locked to the intramedullary nail in accordance with an illustrative embodiment.

FIG. 11 is a cross-sectional side view of the intramedullary nail 100 of FIG. 2 in the un-deployed state. In accordance with the illustrative embodiment, a femoral neck nail or proximal anchor 200 is configured to be received in the lateral through-hole 106 to provide proximal locking of the nail body 104 to the femur bone. This is best seen in FIG. 15. The lateral through-hole 106 may be provided at an angle relative to the nail body 104. In particular, the lateral through-hole 106 may be ±10°, ±20°, ±30°, ±40°, ±50°, or ±60° off perpendicular. The received neck nail or anchor 200 may be locked in the through-hole 106 by a press-fit type connection.

In an alternative embodiment, the received neck nail or anchor 200 may be locked to through-hole 106 (thus nail body 104) by an optional locking screw 118. Although the locking screw 118 is exemplified in the embodiments herein, the locking screw 118 may be omitted, for example, if the anchor 200 is secured in the through-hole 106 by a press-fit or other suitable securing mechanism. By way of example, if present, the locking screw 118 may be rotated towards through-hole 106 to secure the anchor 200 in the through-hole 106. Locking screw 118 is located above through-hole 106 and has an outer surface that is arranged with threads, which are adapted to be threaded against the threads arranged on an inner surface of nail body 104. As shown in FIG. 11, only a small portion of the inner surface of nail body 104 may arranged with threads so as to restrict the longitudinal movement of locking screw 118 within nail body 104.

More specifically, locking screw 118 may be threaded (e.g., clockwise or counter-clockwise) by a locking tool that enters from an opening arranged at a proximal portion of nail body 104. The locking tool can be an electrically powered tool or a non-electrically powered tool (e.g., manual). In either case, because the size of the head is smaller than the through-hole of drive screw 120, the head of the locking tool is able to pass through the through-hole, out the other side of drive screw 120, and engage the recess arranged on locking screw 118. Once the head of the locking tool is received by the recess, the surgeon can rotate locking screw 118 so that an underside of the locking screw engages the outer surface of femur neck screw 200. This effectively locks proximal anchor 200 to nail body 104, thereby providing proximal locking of the nail body to the femur bone. In the illustrative embodiment, the shape of the tool head and the recess is torx-shaped. However, other shapes can be used without departing from the scope of the invention so long as both the tool head and the recess have a complementary shape. The proximal anchor 200 may be locked to the nail body 104 before or after distal locking (e.g., deployment of the expandable distal portion 140) of the nail body 104 to the femur bone.

To achieve distal locking of the intramedullary nail 100, adjustment rod 116 is moved longitudinally within the nail body 104. The adjustment rod 116 may be actuated by any suitable actuation member or mechanism. In one embodiment, the adjustment rod 116 may be linearly translated by rotating an actuation member, such as a drive screw 120, housed within the adjustment rod 116 or housed within the nail body 104. Thus, the actuation member may allow for rotational movement to cause linear movement of the adjustment rod 116 (e.g., pulling the adjustment rod 116 toward the actuation member). It is envisioned, however, that any suitable mechanical actuation mechanism may be selected in order to linearly translate the adjustment rod 116 proximally or distally with respect to the nail body 104. In addition, if desired, a ratcheting mechanism or the like may be used to cause for movement in a single direction. The movement of adjustment rod 116 will now be discussed in more detail in accordance with the embodiment illustrated.

Figure 16:
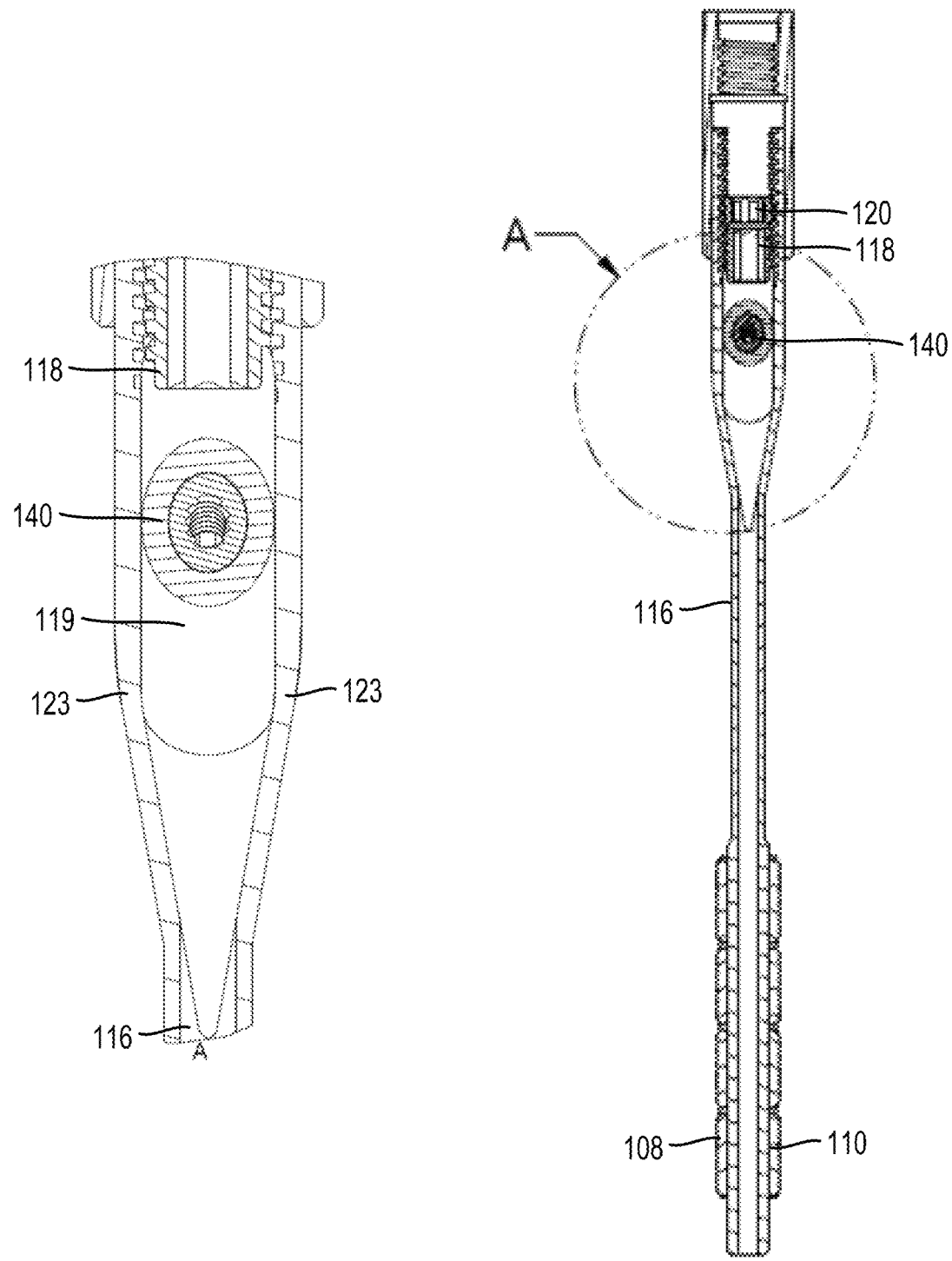
FIG. 16 is a zoomed-in view of section "A" of the intramedullary nail in the un-deployed state according to the illustrative embodiment.
Figure 17:
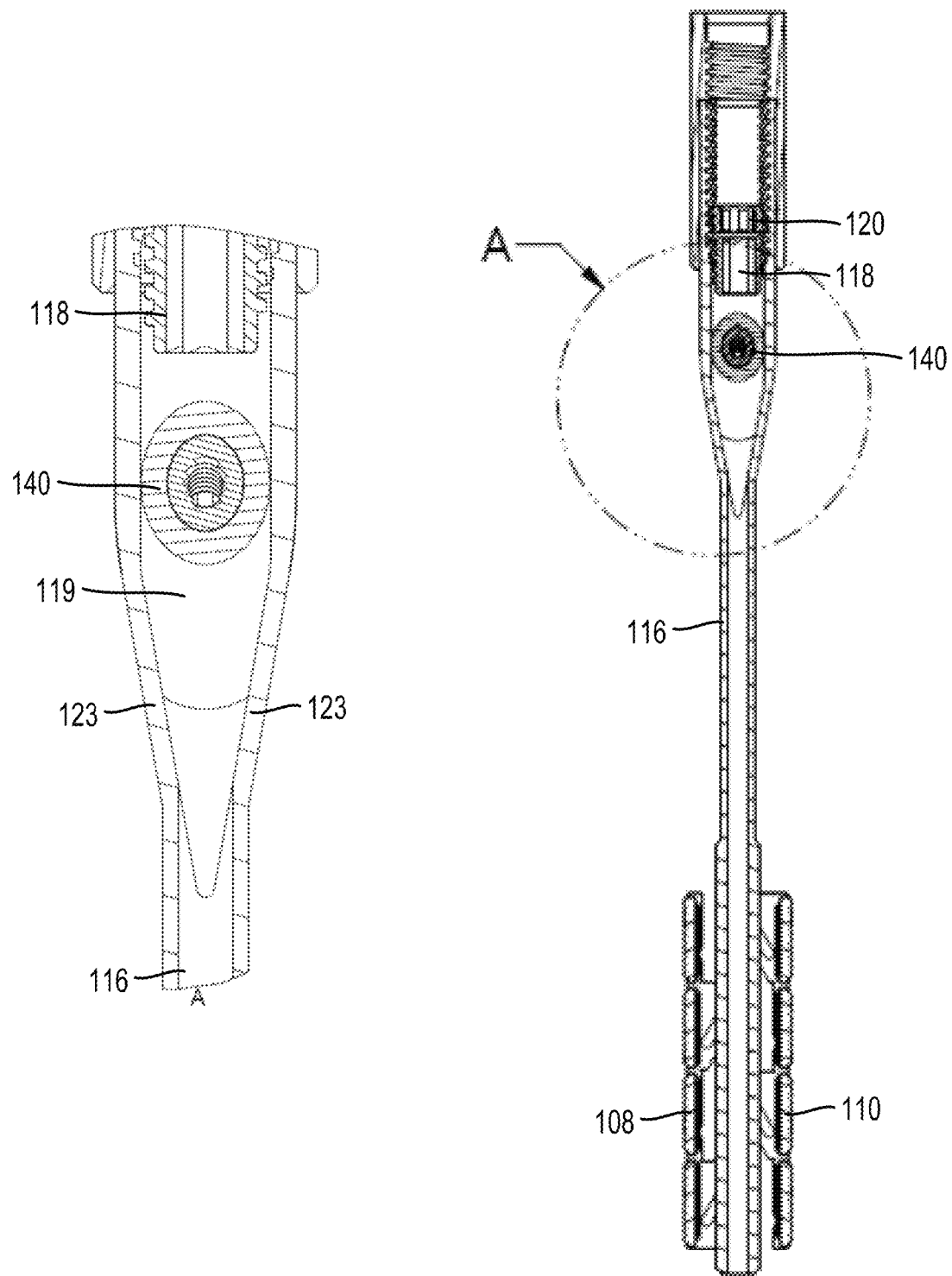
FIG. 17 is a zoomed-in view of section "A" of the intramedullary nail in the deployed state according to the illustrative embodiment.

Adjustment rod 116 is housed within nail body 104. The length of adjustment rod 116 runs from a distal portion of nail body 104 to a proximal portion of nail body 104. The distal portion of adjustment rod 116 is coupled to the first and second fixation members 108, 110, for example, by the tongue-and-groove features described above, with respect to FIGS. 6-8. The proximal portion of adjustment rod 116 has a lateral opening 119 through which locked proximal anchor 200 may be received. The lateral opening 119 has a longitudinal length that is longer than a diameter of the received proximal anchor 200 to allow longitudinal movement of adjustment rod 116 relative to nail body 104. More specifically, and with reference to FIGS. 16 and 17, the proximal portion of adjustment rod 116 has a pair of oppositely positioned extension members 123. The empty space located between the extension members 123 may form the lateral opening 119, which has a longitudinal length that is longer than the diameter of the received proximal anchor 200. In the illustrative embodiment, the pair of oppositely positioned extension members 123 is similar to the U-shaped prongs of a tuning fork, for example. The prongs essentially go around the outer surface of the received proximal anchor 200 and the locking screw 118 so that the adjustment rod 116 can move longitudinally within nail body 104. This can be seen in the close-up portion "A" of FIGS. 16 and 17. It should be noted that locking screw 118 is not threaded to the extension members 123. Rather, locking screw 118 is only threaded to the inner surface of nail body 104. In other embodiments, lateral opening 119 is a through-hole (having a longitudinal length that is longer than the diameter of the received proximal anchor 200) arranged at the proximal portion of adjustment rod 116. In either case, lateral opening 119 allows proximal anchor 200 to enter nail body 104 from one side, pass through adjustment rod 116, and extend out the other side of nail body 104, to anchor into the femur neck.

The inner surface of lateral opening 119 of the adjustment rod 116 may be arranged with threads 122 that are threaded to a drive screw 120. As the drive screw 120 is rotated, the adjustment rod 116 is linear translated toward the drive screw 120. The drive screw 120 may be axially captivated to prevent axial translation while allowing rotation. For example, the drive screw 120 may be adapted to be rotated (e.g., clockwise or counter-clockwise) by a drive tool when resting on shoulder 129 (see FIGS. 13 and 14) of nail body 104, such that rotation of the threaded drive screw 120 causes longitudinal movement of adjustment rod 116 relative to a longitudinal axis of nail body 104. In more detail, drive screw 120 has a longitudinal through-hole that is, for example, and without limitation, torx-shaped. The through-hole of drive screw 120 is adapted to receive a correspondingly shaped head of a drive tool that enters from an opening arranged at a proximal portion of nail body 104. The drive tool can be an electrically powered tool or a non-electrically powered tool (e.g., manual). In either case, once the tool head is received in the recess, drive screw 120 is rotatable by the surgeon. When rotated, the threads arranged on the outer surface of drive screw 120 are threaded against threads 122 of the lateral opening 119 of the adjustment rod 116. As the drive screw 120 is being rotated, an underside of the drive screw 120 rotatably abuts against shoulder 129. In the illustrative embodiment, the shoulder is formed by the difference in diameter between the space occupied by drive screw 120 and the space occupied by locking screw 118. As shown in more clearly in FIGS. 13 and 14, the diameter of the space occupied by drive screw 120 is larger than that of locking screw 118. Thus, it can be said that shoulder 129 is formed by the transition in diameter difference between these two spaces.

Since the space occupied by drive screw 120 may be smaller than the space occupied by locking screw 118, the diameter of drive screw 120 may also smaller than the diameter of locking screw 118. Alternatively, the space occupied by locking screw 118 may be smaller than the space occupied by drive screw 120, the diameter of the locking screw 118 may also smaller than the diameter of drive screw 120. This can be seen more clearly in FIGS. 13 and 14. As briefly discussed above, the surgeon can access locking screw 118 by using a locking tool. The locking tool is smaller than the diameter of the longitudinal through-hole of drive screw 120 and, because of this, the locking tool is able to pass through the longitudinal through-hole of drive screw 120 and be received by a recess of locking screw 118.

The threaded locking screw 118 is adapted to be threaded towards the received proximal anchor 200 by the locking tool to lock the proximal anchor 200 to nail body 104, as discussed above with respect to FIG. 11.

Depending on the direction of rotation of drive screw 120, adjustment rod 116 either moves longitudinally towards the proximal portion or the distal portion of nail body 104. In accordance with the illustrative embodiment, driving adjustment rod 116 from a distal portion of nail body 104 to the proximal portion of the nail body in the manner discussed above causes fixation members 108, 110 to radially deploy out of openings 112, 114, respectively. This can be seen in FIG. 12 when compared to FIG. 11. When fixation members 108, 110 are radially deployed from nail body 104, the teeth arranged on their outer surface 132 contact the inner surface of the intramedullary canal (e.g., engage the cortical bone). On the other hand, driving adjustment rod 116 from the proximal portion of nail body 104 to the distal portion of the nail body in the manner discussed above causes fixation members 108, 110 to radially retract into openings 112, 114, respectively. This can be seen by comparing FIG. 12 to FIG. 11.

Figure 13:
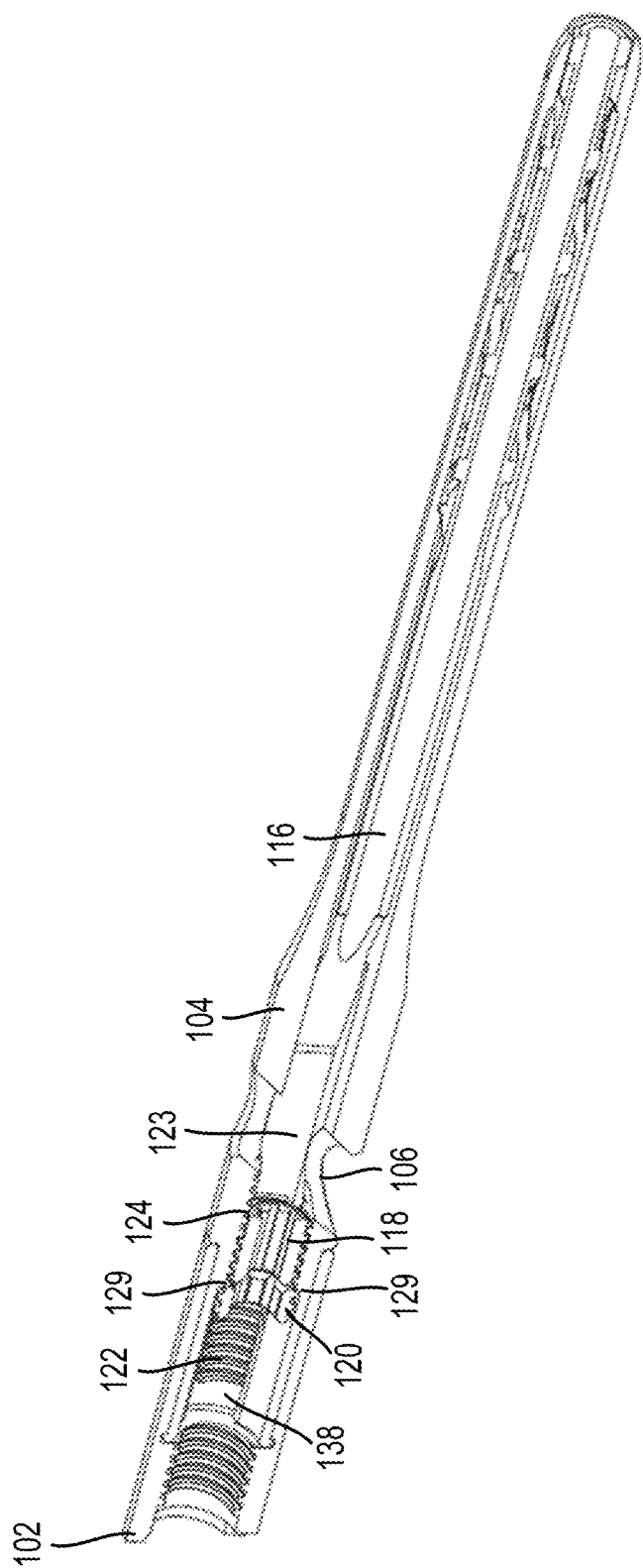
FIG. 13 is a cross-sectional side view of the intramedullary nail of FIG. 11 rotated 90°.
Figure 14:
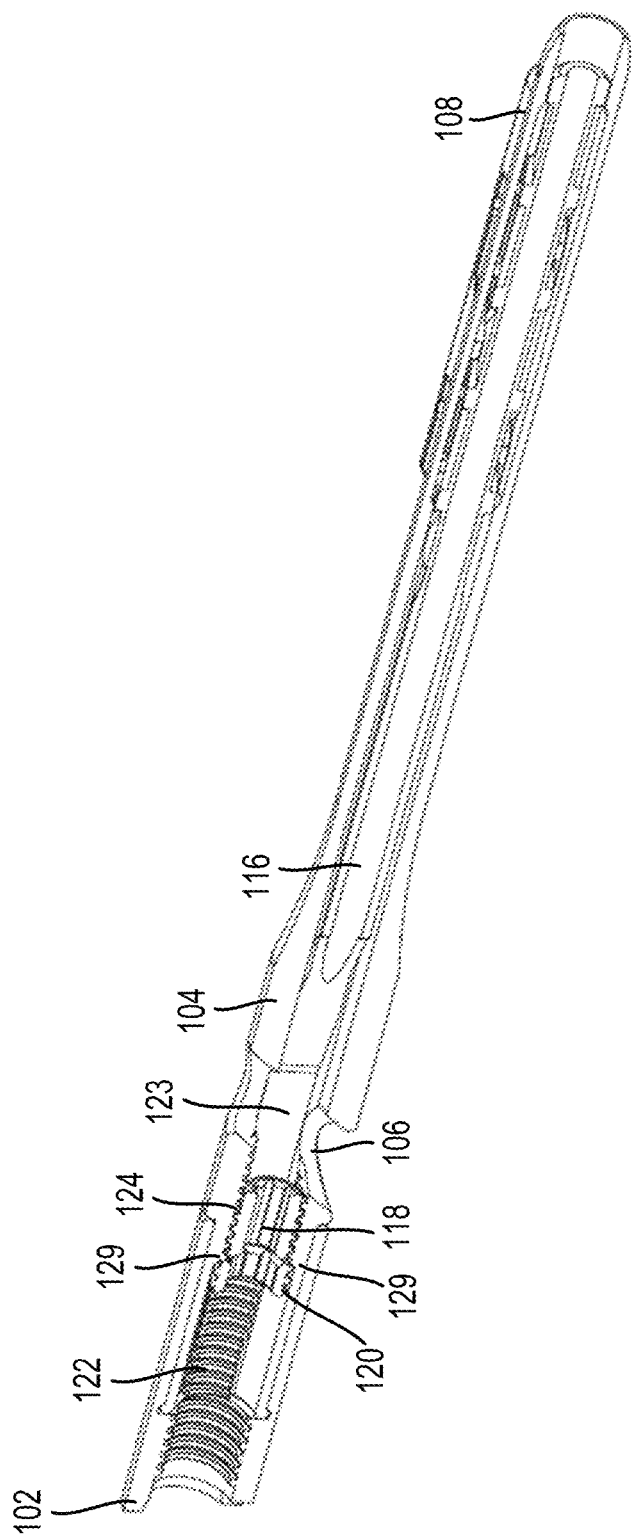
FIG. 14 is a cross-sectional side view of the intramedullary nail of FIG. 12 rotated 90°.

As best seen in FIGS. 11 and 13, the nail body 104 may be arranged with a pair of oppositely positioned grooves 138 that are sized and shaped to receive a respective one of extension members 123 to prevent axial rotation of adjustment rod 116. In the illustrative embodiment, each of the grooves 138 is longer than its respective extension member 123. This configuration allows the extension members to slide back and forth within their respective groove 138 when adjustment rod 116 moves longitudinally within nail body 104, as discussed above. For example, when adjustment rod 116 is driven towards the proximal end of nail body 104 by the drive tool, each extension member 123 will slide in the same direction in their respective groove 130. This can be seen more clearly by comparing FIG. 11 to FIG. 12.

Thus, the adjustment rod 116 actuates the expandable distal portion 140 of the intramedullary nail 100, for example, in the form of one or more fixation members 108, 110, in order to achieve distal locking in the intramedullary canal. After the intramedullary nail 100 has been positioned in the long bone in an un-deployed position, the intramedullary nail 100 can be actuated to expand or deploy the expandable distal portion 140 to the deployed position. The distal end of the nail 100 expands to create a press-fit in the inner area of the intramedullary canal, thereby securing or anchoring the intramedullary nail 100 in position.

Expandable Anchor

Figure 18:
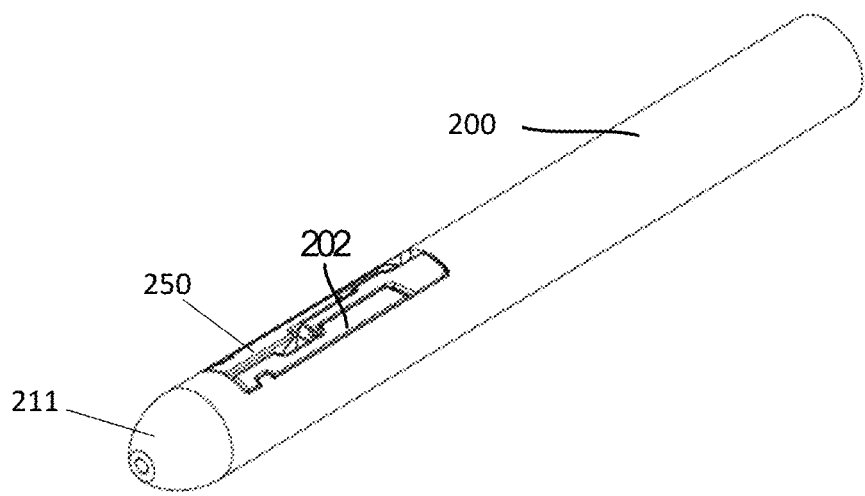
FIG. 18 is a perspective view of the proximal anchor in an un-deployed state according to an illustrative embodiment.
Figure 21:
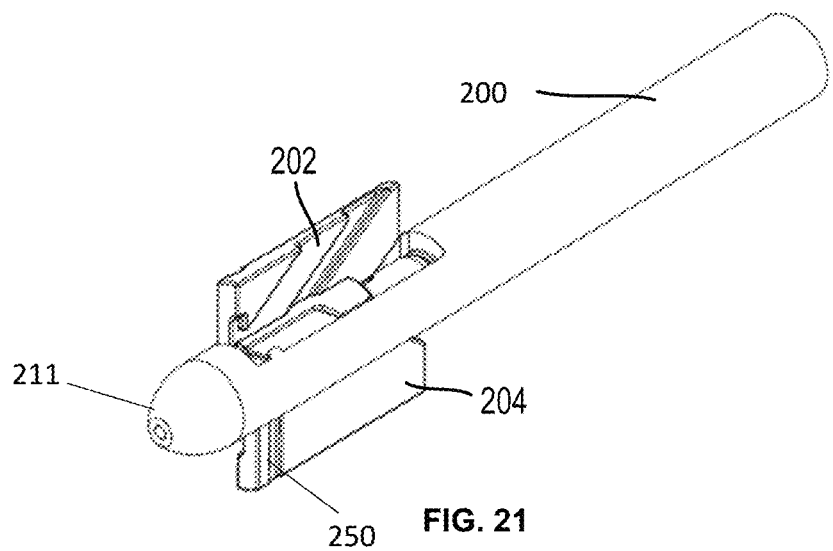
FIG. 21 is a perspective view of the proximal anchor of FIG. 18 in a deployed state according to an illustrative embodiment.

According to one embodiment, the expandable anchor 200 includes an expandable distal portion 250 in order to achieve distal locking of the expandable anchor 200. The expandable anchor 200 is configured to be inserted transverse or crosswise into the intramedullary canal of a long bone while in a contracted or un-deployed state. In particular, the expandable anchor 200 may be especially configured to be at least partially inserted at an angle into the neck of the long bone (e.g., the femoral neck of a femur). FIG. 18 is a perspective view of one version of the expandable anchor 200 in an un-deployed state. After the expandable anchor 200 has been positioned in the long bone, the expandable anchor 200 can be actuated, for example, using mechanical actuation, to expand or deploy the expandable distal portion 250 to an expanded or deployed state. FIG. 21 is a perspective view of the expandable anchor 200 in a deployed state.

Traditional hip screws or proximal femoral nails may require the placement of an anchor or lag screw into the femoral neck to prevent femoral head cut-through and to aid in rotational stability and fracture reduction. Historically, this has been accomplished with one large bolt, multiple smaller screws, or a helical blade, for example. Traditional concepts may be limited, however, in the available diameter by the diameter of the hole in the proximal nail. To meet this and other needs, expandable intramedullary systems are provided that have integrated distal locking and/or proximal locking, which are designed to prevent rotation and/or axial movement of the intramedullary nail once implanted.

Figure 19:
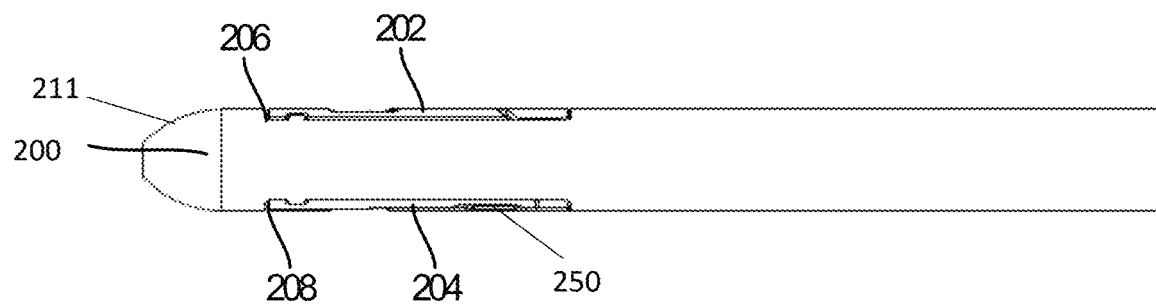
FIG. 19 is a side view of the proximal anchor nail of FIG. 18 in accordance with an illustrative embodiment.
Figure 20:
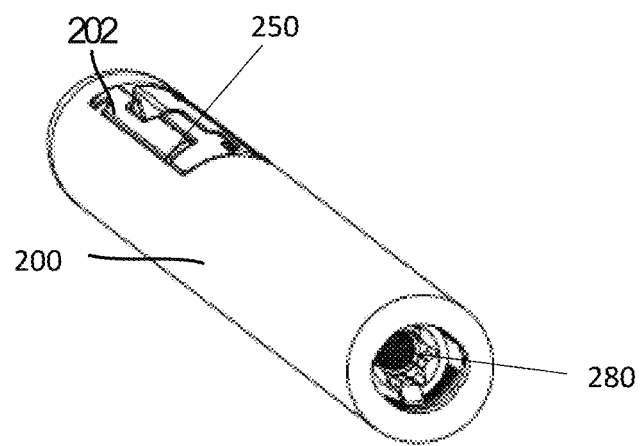
FIG. 20 is a back perspective view of the proximal anchor of FIG. 18 in accordance with an illustrative embodiment.
Figure 22:
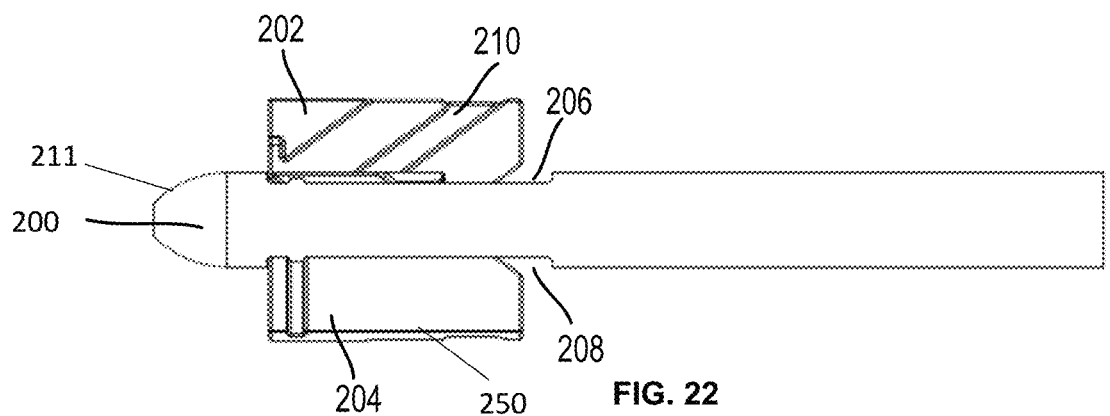
FIG. 22 is a side view of the proximal anchor of FIG. 21 in accordance with an illustrative embodiment.
Figure 23:
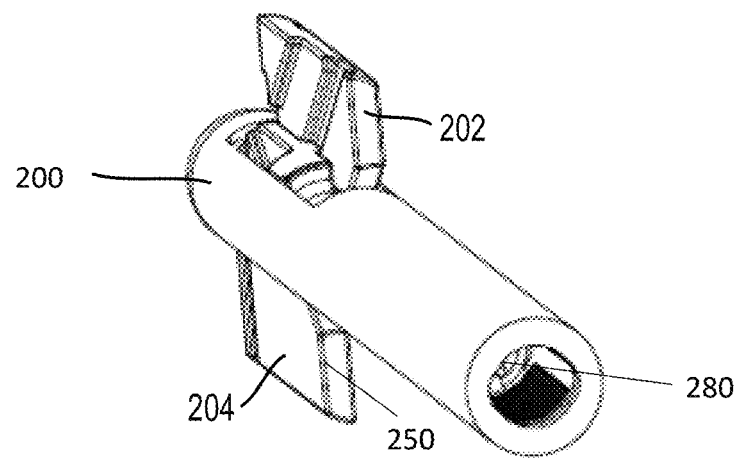
FIG. 23 is a back perspective view of the proximal anchor of FIG. 21 in accordance with an illustrative embodiment.

To cure at least some deficiencies of traditional anchors, the proximal anchor 200 is provided with one or more expandable or deployable securing members 202, 204 (e.g., a pair of securing members 202, 204) that are able to retract into the axial profile of the proximal anchor 200 for insertion (e.g., <∅7.5 mm on a ∅7.5 mm anchor), as shown in FIGS. 18-20. After insertion, the securing members 202, 204 are able to expand radially into the femoral neck, as shown in FIGS. 21-23. Unlike other devices which may use a shape-memory alloy or other shape-memory technique for the securing members to automatically deploy from the device, the expandable anchor 200 is configured such that the expandable distal portion 250 expands outwardly from the anchor 200 with continuous and/or discrete adjustments. In other words, the expandable distal portion 250 is uniquely controlled such that the securing members 202, 204 can be deployed to any desired amount without requiring full deployment. Thus, the securing members 202, 204 can be deployed to the degree necessary to achieve the desired press-type fit connection without providing too much stress on the bone. In addition, unlike other devices which may use an inflatable device or cavity, for example, filled with bone cement or the like in order to expand a portion of the anchor, the expandable anchor 200 relies on one or more mechanically actuated mechanisms to expand the expandable distal portion 250. Due to the mechanical functionality of the securing members 202, 204, the overall length of the anchor 200 does not change when the securing members 202, 204 are expanded. In addition, the dimensions of the securing members 202, 204 do not change or alter when they are expanded (although more of the securing members 202, 204 protrude from the anchor 200 when expanded or deployed).

In the embodiment shown in FIGS. 18-25, the expandable anchor 200 includes a cannulated elongate body, an actuation mechanism including adjustment member 220 and deployment member 240 extending longitudinally through the elongate body, a first expandable securing member 202, and a second expandable securing member 204. The anchor 200 may terminate in a tip 211. The tip 211 may be rounded, curved, or substantially blunt. The tip 211 of the anchor 200 may house one or more pins 270. When assembled, the pin 270 may engage a recess in the securing members 202, 204 in the contracted position. When fully deployed, the pin 270 may engage a portion of the deployment member 240.

As shown in FIGS. 21-23, the securing members 202, 204 extend from a distal portion of the body of the anchor 200 when deployed. The body of the proximal anchor 200 has slots 206, 208 cut out at the distal portion of the proximal anchor 200 where at least two expandable securing members 202, 204 are inserted and extend therethrough in the expanded position. In accordance with the illustrative embodiment, each of the expandable securing members 202, 204 is a rectangular-shaped paddle, plate, etc. In this embodiment, the securing members 202, 204 have a plate-like or elongated shape. In particular, the securing members 202, 204 have a length greater than their width. The securing members 202, 204 may extend a suitable distance from the body of the anchor 200. The securing members 202, 204 may be positioned at any suitable location along the length of the anchor 200. Preferably, the securing members 202, 204 are positioned at a distal-most end of the anchor 200, for example, proximate to the tip 211. It is envisioned, however, that additional securing members 202, 204 may be provided along the length of the anchor 200, for example, substantially centrally along the length or closer to the proximal portion.

Figure 24:
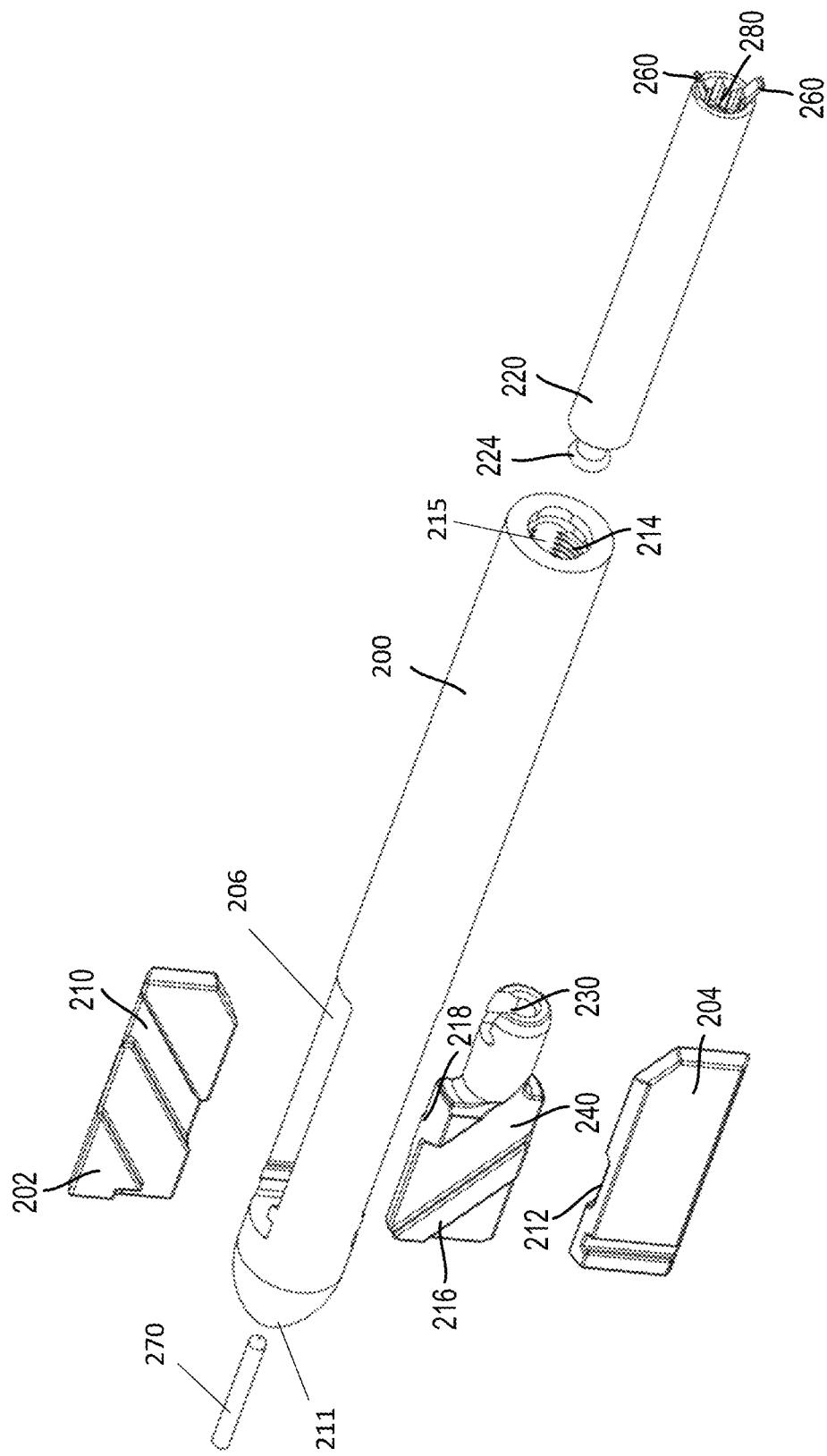
FIG. 24 depicts the elements that form the proximal anchor in accordance with an illustrative embodiment.
Figure 25:
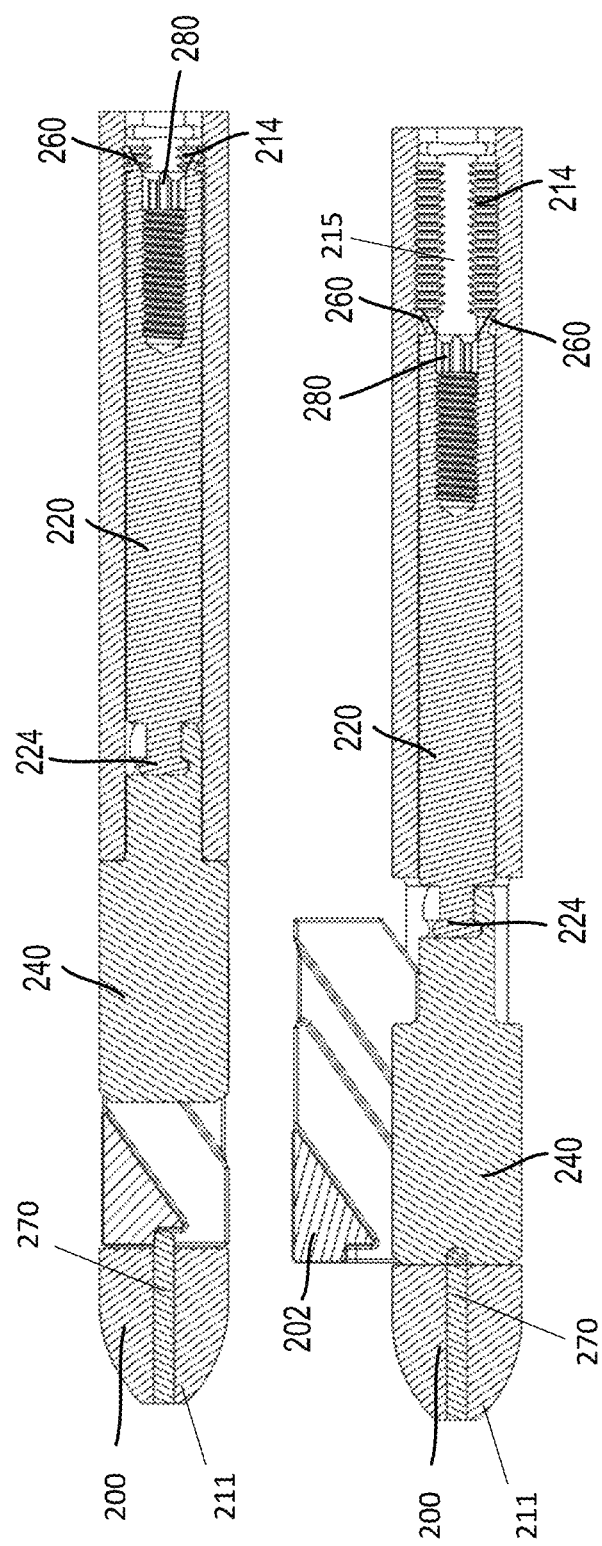
FIG. 25 is a cross-sectional view of the proximal anchor in an un-deployed and deployed state in accordance with an illustrative embodiment.

Each of the securing members 202, 204 interfaces with a deployment mechanism 240 that is coupled to an adjustment member 220 disposed within the body of the proximal anchor 200. If desired, the adjustment member 220 and deployment mechanism 240 could be integrated as one monolithic member. As shown in FIG. 24, the deployment mechanism 240 is coupled to the adjustment member 220 by positioning head 224 into slot 230. In particular, the head 224 may be slid into slot 230 of the deployment mechanism 240 in order to interconnect the adjustment member 220 and the deployment mechanism 240.

The deployment mechanism 240 interfaces with the securing members 202, 204 such that linear movement of the deployment mechanism 240 causes the securing members 202, 204 to deploy from the anchor 200. Each securing member 202, 204 includes at least one ramp or angled surface having a slope. In particular, an inner surface of each securing member 202, 204 is arranged with at least one ramp or angled surface having a slope or angle relative to the longitudinal axis of the anchor body 200. The ramps or angled surfaces may be in the form of one or more grooves, recesses, projections, protrusions, or the like in the securing members 202, 204. The ramp or angled surface may extend from a first end of the securing member 202, 204 to a second, opposite end of the securing member 202, 204. One ramp or multiple ramps or angled surfaces may be provided for securing member 202, 204. In one embodiment, the deployment mechanism 240 is coupled to securing member 204 by sliding tongue 216 into groove 212 of securing member 204. Similarly, the deployment mechanism 240 may be coupled to securing member 202 by sliding angled tongue 218 into groove 210 of securing member 202.

It is contemplated that the slope of the ramped surfaces on securing member 202, 204 can be equal or can differ from one another. The ramps can serve to move the securing members 202, 204 when the deployment mechanism 240 is linearly translated between the securing members 202, 204. For example, as the deployment mechanism moves distally, the ramped surfaces 216, 218 of the deployment mechanism 240 push against the ramped surfaces 210, 212 of the securing members 202, 204 pushing the securing members 202, 204 outwardly into the expanded position. It should also be noted that the expansion of the securing members 202, 204 can be varied based on the differences in the dimensions of the ramped surfaces.

The adjustment member 220 is adapted to be driven along a longitudinal axis of proximal anchor 200 while coupled to deployment mechanism 240. More specifically, when adjustment member 220 is coupled to deployment mechanism 240 and disposed within the body of the anchor 200, a tool may be inserted into a recess 280 (e.g., a torx-shaped) in the proximal end of the anchor 200. As an axial force is applied to the adjustment member 220, the adjustment member 220 and deployment mechanism 240 are driven towards the distal portion of proximal anchor 200, as shown in the bottom view of FIG. 25. When adjustment member 220 and deployment mechanism 240 are advanced towards the distal portion of anchor 200 by the tool, tongues 216, 218 slide along grooves 210, 212, respectively, to force the securing members 202, 204 to radially deploy from their respective openings 206, 208.

One or more angled projections 260 are configured to engage partial threads 214 arranged on an inner surface of proximal anchor 200 to provide for ratchet-like advancement of the adjustment member 220, deployment mechanism 240, and corresponding securing members 202, 204. The angled projections 260 prevent the adjustment member 220 from moving towards the proximal end of the anchor 200 when engaged with the threads 214 on the interior of the anchor 200. The angled projections 260 may be positioned on a proximal-most end of the adjustment member 220 or at any suitable location along the length of the adjustment member. As shown, two opposite angled projections 260 may be provided to engage with two threaded portions 214 located inside the anchor 200. Any suitable number of angled projections 160 may be provided in any desirable orientation.

In the event that the securing members 202, 204 need to be retracted or collapsed back into the body of the anchor 200 (e.g., to adjust the position or remove the anchor 200), the adjustment member 220 may be rotated (e.g., about 90°) such that the angled projections 260 no longer align with the threads 214 on the inner surface of the anchor 200. In other words, the adjustment member 220 is rotated such that the angled projections 260 align with at least one smooth portion 215 on the inner surface of the anchor 200 such that the adjustment member 220 is permitted to move proximally, thereby allowing the securing members 202, 204 to retract. In order to rotate the adjustment member 220, a tool may be threaded into the internal threads of the adjustment member 220.

Although two securing members 202, 204 are shown, it is envisioned that any suitable number, size, and type of securing members may be selected to obtain the desired fixation and press-fit type anchoring when deployed or expanded in the bone. In particular, the expandable distal portion 250 may include one or more plates, projections, extensions, spikes, teeth, pointed members, or the like configured to emerge from within the body of the expandable anchor 200. Moreover, the securing members 202, 204 may be generally flat, contoured, provided with surface roughening or teeth, or have any characteristics to enhance locking of the distal portion 250 of the expandable anchor 200 when expanded. Moreover, the securing members 202, 204 may be offset and parallel, in-line and parallel, non-parallel, radially extending around the periphery of the anchor, or of any other suitable configuration. Thus, there can be more than two securing members, at various angles, and either inline or offset to varying degrees. The securing members 202, 204 may deploy or move out radially without axial translation or rotation of the securing member 202, 204 themselves. It is also envisioned that the securing members 202, 204 may be configured to provide for axial translation and/or rotation as well.

It should be appreciated that the role of the expandable mechanisms of the proximal anchor 200 and intramedullary nail 100 can be reversed. More specifically, according to a further embodiment, the proximal anchor 200 may be adapted to be inserted into the intramedullary canal of a femur shaft to provide distal locking, while the nail 100 may be adapted to be inserted into the femur neck. Also, as described elsewhere herein, the intramedullary system 10 including the expandable intramedullary nail 100 and expandable anchor 200 may be used for any suitable bones or long bones. Thus, even though the description generally refers to treatment of a femur, the systems, devices, and methods may be equally applied to any other long or hollow bone structure. It is also contemplated that the expansion mechanisms described herein may have applicability in other areas including those outside of long bone applications.

Trochanteric Nail

Figure 26:
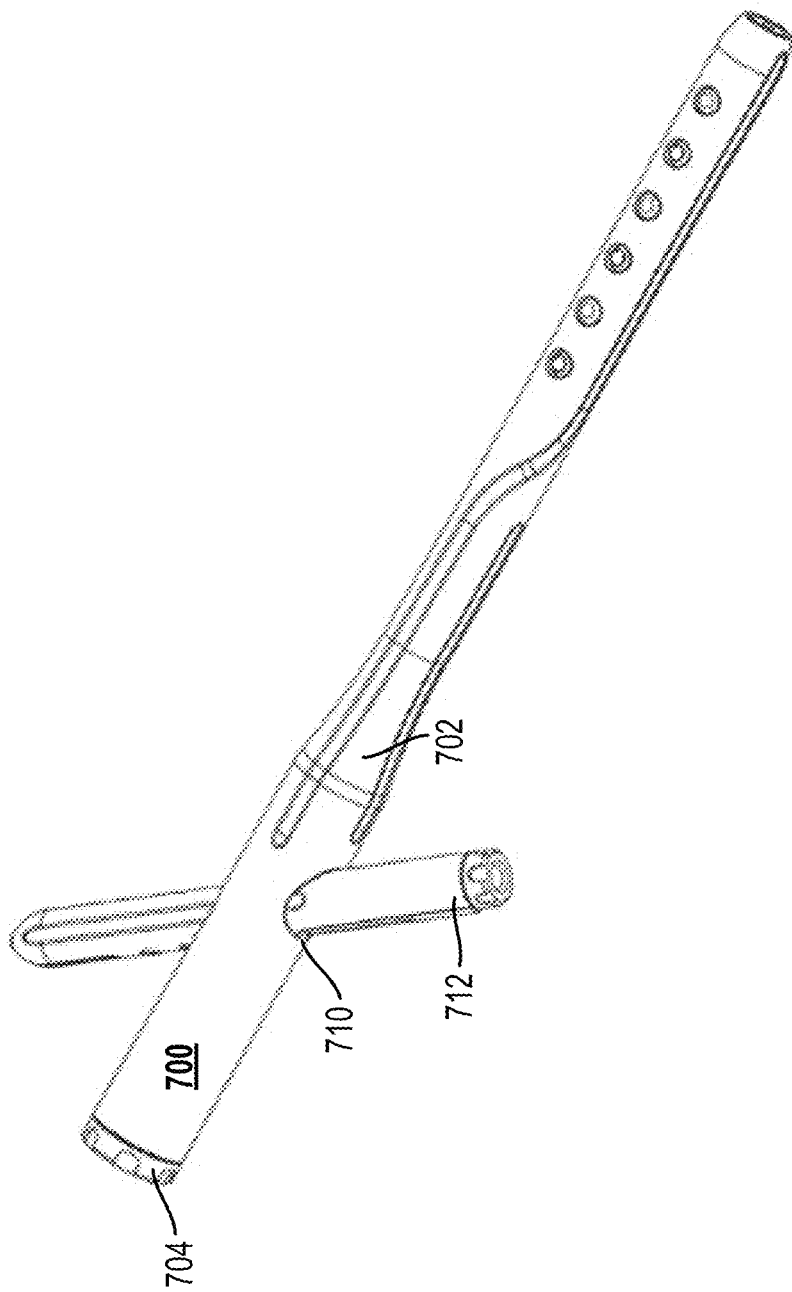
FIG. 26 is a perspective view of an intramedullary nail in an un-deployed state according to an alternative embodiment.
Figure 27:
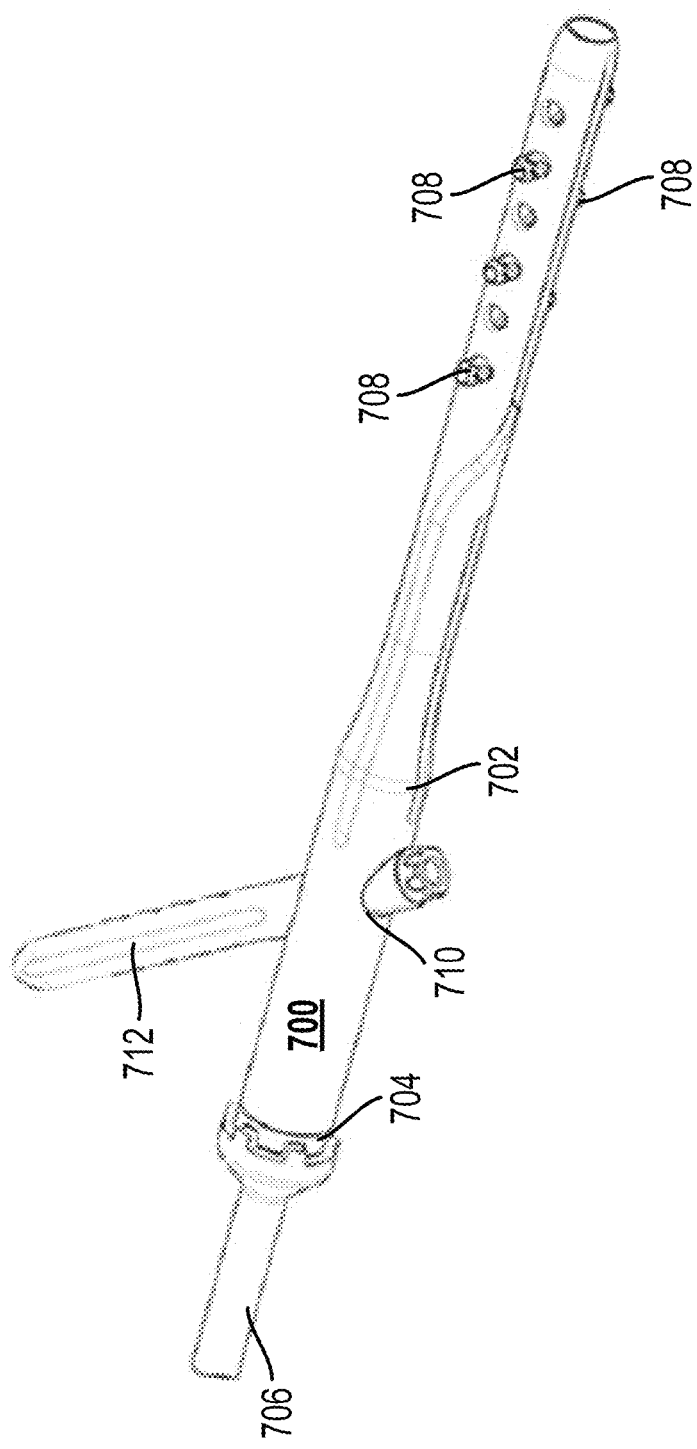
FIG. 27 is a perspective view of the intramedullary nail of FIG. 27 in a deployed state according to an alternative embodiment.

FIG. 26 depicts a trochanteric nail 700 in an un-deployed state in accordance with an alternative embodiment. Trochanteric nail 700 has end cap 704 that is adapted to receive a tool 706, as shown in FIG. 27. The tool is adapted to provide distal locking by rotating end cap 704 to radially deploy spikes 708 from body 702. The spikes 708 are adapted to engage the inner surface of an intramedullary canal in which nail 700 is implanted. Body 702 also includes through-hole 710 that is sized and shaped to receive a femur neck nail 712 adapted for proximal locking. Femur neck nail 712 is essentially a smaller size of trochanteric nail 700, wherein femur neck nail 712 has the same elements and functions as trochanteric nail 700. Therefore, those skilled in the art will appreciate that the following discussion of trochanteric nail 700 equally applies to femoral neck nail 712.

Figure 28:
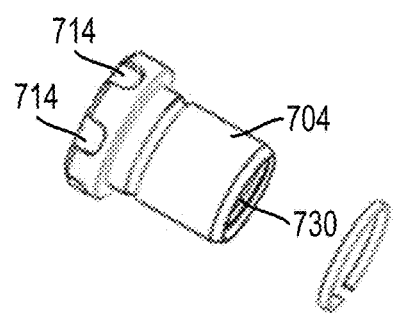
FIG. 28 is a perspective view of an end cap adapted to be threaded to the intramedullary nail of FIG. 27 according to an alternative embodiment.
Figure 29:
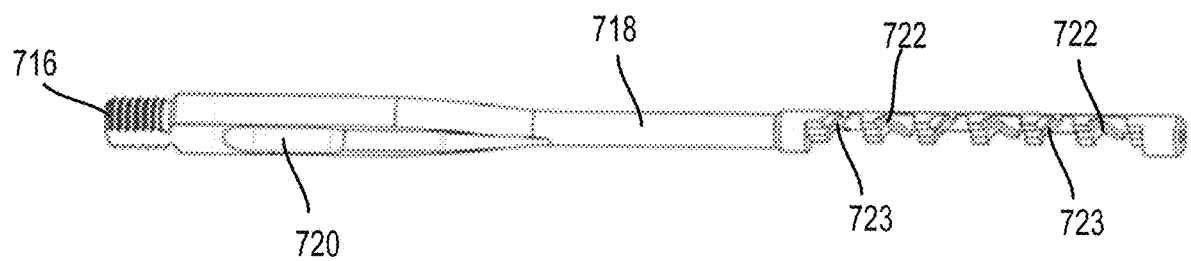
FIG. 29 is a perspective view of an adjustment rod disposed within the intramedullary nail of FIG. 27 according to an alternative embodiment.

FIG. 28 shows end cap 704 having holder retaining features 714 for receiving a correspondingly size and shaped projection arranged on the head of tool 706. End cap 704 has a threaded inner surface 730 so that it can be threaded to the threaded end 716 of the adjustment rod 718 depicted in FIG. 29. The adjustment rod 718 is housed within nail body 702 and adapted to move longitudinally within the nail body. Similar to adjustment rod 116 at the beginning of this disclosure, FIG. 29 shows adjustment rod 718 having a lateral opening 720, which has a longitudinal length that is longer than the diameter of femoral neck nail 712. The lateral opening 720 allows femoral neck nail 712 to pass through nail body 702 of trochanteric nail 700, while still allowing adjustment rod 718 to longitudinally move within nail body 702.

Figure 30:
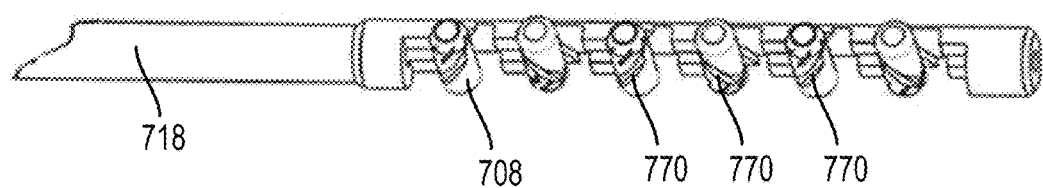
FIG. 30 is a perspective view of a captivator adapted to couple to the adjustment rod of FIG. 29 according to an alternative embodiment.
Figure 30:
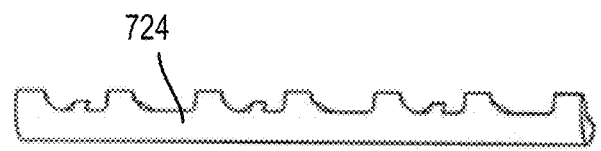

As further shown in FIG. 29, the distal portion of adjustment rod 718 is arranged with a first plurality of articulating ramps 722 and a second plurality of articulating ramps 723. Articulating ramps 722 radially deploy spikes 708 in one direction while the second plurality of articulating ramps 723 deploy other spikes 708 in the other direction, as shown in FIG. 27. Each of the articulating ramps 722 is adapted to be received by an articulating slot 770 arranged on the outer surface of spike 708. The articulated slot can be seen in FIG. 30. Once received, a captivator 724 is fitted onto the distal portion of adjustment rod 718. When end cap 704 is rotated (e.g., clockwise or counter-clockwise) by tool 706, adjustment rod 718 move towards the proximal portion of body 702, thereby causing each spike 708 to engage captivator 724. In response to engaging captivator 724, the first and second plurality of articulating ramps 722, 723 slide along their articulating slots 770 arranged on spikes 708, which then forces each of the spikes to be radially deployed from body 702 through their respective openings 730. Spikes 708 contact an inner surface of the intramedullary canal to provide distal locking.

Although the invention has been described in detail and with reference to specific embodiments, it will be apparent to one skilled in the art that various changes and modifications can be made without departing from the spirit and scope of the invention. Thus, it is intended that the invention covers the modifications and variations of this invention provided they come within the scope of the appended claims and their equivalents. It is expressly intended, for example, that all ranges broadly recited in this document include within their scope all narrower ranges which fall within the broader ranges. It is also intended that the components of the various devices disclosed above may be combined or modified in any suitable configuration.

What is claimed is:

1. A method for stabilizing a long bone, the method comprising:
    inserting an expandable intramedullary nail into an intramedullary canal of a long bone in a contracted position, the intramedullary nail having a proximal portion and a distal portion, the proximal portion having an opening extending therethrough and the distal portion having one or more expandable fixation members disposed in the intramedullary nail, one of the one or more expandable fixation members extending from a first end to a second end along a longitudinal axis of the intramedullary nail;
    inserting a proximal anchor through the opening in the intramedullary nail and substantially transverse to the intramedullary nail to securely anchor the proximal portion of intramedullary nail; and
    deploying the one or more fixation members to an expanded position by mechanical actuation of the expandable intramedullary nail such that the one or more fixation members radially extend from the intramedullary nail to securely anchor the distal portion of intramedullary nail in the intramedullary canal, wherein, when deployed, each of the first end and the second end of the expandable fixation member is extended outwardly the same distance from the longitudinal axis of intramedullary nail;
    wherein the expandable intramedullary nail includes an adjustment rod having a ramped surface that engages a ramped surface of at least one of the fixation members, the adjustment rod having a pair of proximal extension members that define a lateral opening that communicates with the opening in the intramedullary nail such that the lateral opening receives the proximal anchor;
    wherein the expandable intramedullary nail includes a securing mechanism that is engaged with an actuation mechanism in a contracted position and the expanded position.

2. The method of claim 1, wherein the intramedullary nail further includes an actuation member, wherein the one or more fixation members are deployed by moving the adjustment rod longitudinally through the nail body.

3. The method of claim 2, further comprising rotating the actuation member positioned within the adjustment rod to linearly translate the adjustment rod.

4. The method of claim 2, wherein a distal portion of the adjustment rod is arranged with a plurality of angled tongues or grooves configured to engage with corresponding angled grooves or tongues on the one or more fixation members, and wherein translational movement of the adjustment rod causes the one or more fixation members to deploy to the expanded position.

5. The method of claim 4, wherein the plurality of angled tongues or grooves include at least two angled ramps spaced apart from one another and angled in the same direction.

6. The method of claim 1, further comprising expanding the proximal anchor.

7. The method of claim 6, wherein a distal portion of the proximal anchor has one or more expandable securing members disposed in the proximal anchor in a contracted position, wherein, upon mechanical actuation of the one or more securing members, the one or more securing members radially extend from the proximal anchor to an expanded position to securely anchor the proximal portion of intramedullary nail.

8. The method of claim 6, wherein the proximal anchor includes a cannulated elongate body, an anchor actuation mechanism for the proximal anchor extending longitudinally through the elongate body, and at least one expandable securing member engaged with the anchor actuation mechanism, wherein upon linear movement of the anchor actuation mechanism, the at least one securing member deploys from the elongate body.

9. The method of claim 8, wherein the anchor actuation mechanism includes an adjustment member connected to a deployment member, and wherein the at least one securing member deploys into the expanded position when an axial force is applied to the adjustment member.

10. The method of claim 9, wherein the deployment member is arranged with at least one angled tongue or groove configured to engage with a corresponding angled groove or tongue on the at least one securing member, and wherein translational movement of the deployment member causes the at least one securing member to deploy to the expanded position.

11. The method of claim 1, wherein the one or more expandable fixation members deploy from the intramedullary nail with continuous and discrete adjustments.

12. The method of claim 1, wherein the long bone is a femur, tibia, fibula, humerus, radius, ulna, or phalange.

13. A method for stabilizing a long bone, the method comprising:
inserting an expandable intramedullary nail into an intramedullary canal of a long bone, the expandable intramedullary nail comprising an elongate nail body having a proximal portion and a distal portion, an elongate adjustment rod extending through the nail body, and an actuation member, the proximal portion having an opening extending therethrough, and the distal portion having one or more expandable fixation members disposed in the nail body in a contracted position, one of the one more expandable fixation members extending from a first end to a second end along a longitudinal axis of expandable the intramedullary nail;
inserting an expandable proximal anchor through the opening and transverse to the expandable intramedullary nail to secure the proximal portion of the expandable intramedullary nail; and
deploying the expandable fixation members by rotating the actuation member, thereby causing the adjustment rod to linearly translate through the nail body, and the one or more fixation members to radially extend from the expandable intramedullary nail to an expanded position to securely anchor the distal portion of intramedullary nail in the intramedullary canal, wherein, when deployed, each of the first end and the second end of the expandable fixation member is extended outwardly the same distance from the longitudinal axis of intramedullary nail,
wherein the elongate adjustment rod includes a ramped surface that engages a ramped surface of at least one of the fixation members, the elongate adjustment rod having a pair of proximal extension members that define a lateral opening that communicates with the opening in the intramedullary nail such that the lateral opening receives the proximal anchor;
wherein the expandable intramedullary nail includes a securing mechanism that is engaged with an actuation mechanism in a contracted position and the expanded position.

14. The method of claim 13, wherein a distal portion of the elongate adjustment rod is arranged with a plurality of angled tongues or grooves configured to engage with corresponding angled grooves or tongues on the one or more fixation members, and wherein translational movement of the elongate adjustment rod causes the one or more fixation members to deploy to the expanded position.

15. The method of claim 13, wherein the expandable proximal anchor includes a cannulated elongate body, an anchor actuation mechanism for the expandable proximal anchor extending longitudinally through the elongate body, and at least one expandable securing member engaged with the anchor actuation mechanism, and wherein upon linear movement of the anchor actuation mechanism, the at least one securing member deploys from the elongate body.

16. The method of claim 15, wherein the anchor actuation mechanism includes an adjustment member connected to a deployment member, and at least one securing member deploys into the expanded position when an axial force is applied to the adjustment member.

17. The method of claim 16, wherein the deployment member is arranged with at least one angled tongue or groove configured to engage with a corresponding angled groove or tongue on the at least one securing member, and wherein translational movement of the deployment member causes the at least one securing member to deploy to the expanded position.

18. The method of claim 16, wherein the adjustment member includes one or more angled projections configured to engage partial threads arranged on an inner surface of the proximal anchor to provide for advancement of the adjustment member.

19. The method of claim 18, further comprising rotating the adjustment member such that the angled projections align with at least one smooth portion on the inner surface of proximal anchor, thereby permitting the adjustment member to move proximally and allowing the at least one securing member to retract.

20. A method for stabilizing a long bone, the method comprising:
inserting an expandable intramedullary nail into an intramedullary canal of a long bone, the expandable intramedullary nail comprising an elongate nail body having a proximal portion and a distal portion, an elongate adjustment rod extending through the nail body, and an actuation member, the proximal portion having an opening extending therethrough, and the distal portion having one or more expandable fixation members disposed in the nail body in a contracted position, one of the one more expandable fixation members extending from a first end to a second end along a longitudinal axis of the expandable intramedullary nail;
inserting an expandable proximal anchor through the opening and transverse to the expandable intramedullary nail, the proximal anchor having a cannulated elongate body, an actuation mechanism extending longitudinally through the elongate body, and at least one expandable securing member engaged with the actuation mechanism;
deploying the one or more expandable fixation members from the expandable intramedullary nail by rotating the actuation member and thereby moving the adjustment rod longitudinally through the nail body, wherein the one or more expandable fixation members radially extend from the intramedullary nail to an expanded position to securely anchor the distal portion of intramedullary nail in the intramedullary canal, wherein, when deployed, each of the first end and the second end of the expandable fixation member is extended outwardly the same distance from the longitudinal axis of intramedullary nail; and deploying the at least one expandable securing member from the elongate body of the anchor by linear movement of the actuation mechanism, wherein the at least one expandable securing member radially extends from the anchor to an expanded position to securely anchor the proximal portion of intramedullary nail in the intramedullary canal;

wherein the adjustment rod includes a ramped surface that engages at least one of the expandable fixation members, the adjustment rod having a pair of proximal extension members that define a lateral opening that communicates with the opening in the intramedullary nail such that the lateral opening receives the proximal anchor;

wherein the expandable intramedullary nail includes a securing mechanism that is engaged with an actuation mechanism in a contracted position and the expanded position.

* * * * *